(12) United States Patent
Lingane

(10) Patent No.: US 12,345,556 B2
(45) Date of Patent: Jul. 1, 2025

(54) FLOW SENSING DEVICE AND METHOD

(71) Applicant: NVENTION LTD., London (GB)

(72) Inventor: Paul James Lingane, Palomar Park, CA (US)

(73) Assignee: NVENTION LTD., London (GB)

( * ) Notice: Subject to any disclaimer, the term of this patent is extended or adjusted under 35 U.S.C. 154(b) by 0 days.

(21) Appl. No.: 18/674,600

(22) Filed: May 24, 2024

(65) Prior Publication Data
US 2024/0361164 A1    Oct. 31, 2024

Related U.S. Application Data

(63) Continuation of application No. PCT/EP2022/058611, filed on Mar. 31, 2022.
(Continued)

(51) Int. Cl.
*G01F 1/68*   (2006.01)
*A61M 5/168*  (2006.01)
(Continued)

(52) U.S. Cl.
CPC ....... *G01F 1/6847* (2013.01); *A61M 5/16886* (2013.01); *A61M 27/00* (2013.01); *G01F 1/696* (2013.01); *A61M 2205/3334* (2013.01); *A61M 2205/3368* (2013.01); *A61M 2205/3653* (2013.01)

(58) Field of Classification Search
CPC .. G01F 1/6847; G01F 1/696; A61M 5/16886; A61M 27/00; A61M 2205/3334; A61M 2205/3368; A61M 2205/3653
See application file for complete search history.

(56) References Cited

U.S. PATENT DOCUMENTS

| | | | |
|---|---|---|---|
| 6,474,155 B1 * | 11/2002 | Berkcan | G01F 1/6847 |
| | | | 73/204.26 |
| 7,000,464 B2 * | 2/2006 | McMillan | G01F 5/005 |
| | | | 73/204.27 |

(Continued)

FOREIGN PATENT DOCUMENTS

| | | |
|---|---|---|
| DE | 3827444 A1 | 2/1990 |
| EP | 2403558 B1 | 3/2016 |

(Continued)

OTHER PUBLICATIONS

International Search Report (Form PCT/ISA/210) for International Application No. PCT/EP2022/058611 mailed Dec. 8, 2022 (3 pages).

(Continued)

*Primary Examiner* — Freddie Kirkland, III
(74) *Attorney, Agent, or Firm* — Withrow + Terranova, PLLC; Vincent K. Gustafson

(57) ABSTRACT

Embodiments of the invention provide a device and method of action for a device that abuts the outside of infusion or effusion tubing and uses thermal mass-flow techniques to determine if fluid is flowing or stopped within the tubing. The device includes a housing which carries a heater and temperature sensor arranged such that, when the housing is coupled to the tubing, the heater and temperature sensor are at opposite sides of the tubing wall, in facing relationship. They are for example approximately diametrically opposed, permitting the device to contact the tubing at only one point and so be very compact.

18 Claims, 12 Drawing Sheets

Related U.S. Application Data

(60) Provisional application No. 63/283,460, filed on Nov. 28, 2021, provisional application No. 63/266,997, filed on Jan. 21, 2022.

(51) Int. Cl.
*A61M 27/00* (2006.01)
*G01F 1/684* (2006.01)
*G01F 1/696* (2006.01)

(56) References Cited

U.S. PATENT DOCUMENTS

| | | | | |
|---|---|---|---|---|
| 8,784,367 | B2* | 7/2014 | Dekker | G01F 15/005 |
| | | | | 604/890.1 |
| 8,794,081 | B2* | 8/2014 | Haartsen | A61M 5/16886 |
| | | | | 73/204.11 |
| 10,281,308 | B2* | 5/2019 | Roosli | G01F 1/68 |
| 10,788,346 | B2* | 9/2020 | Yamazaki | G01F 1/684 |
| 10,842,950 | B2* | 11/2020 | Peri | A61M 3/0204 |
| 11,150,154 | B2* | 10/2021 | Krywyj | G01N 33/18 |
| 11,181,405 | B2* | 11/2021 | Murakami | G01F 1/662 |
| 11,446,436 | B2* | 9/2022 | List | A61M 5/14248 |
| 11,566,957 | B2* | 1/2023 | Krywyj | G01F 1/66 |
| 11,672,900 | B2* | 6/2023 | Peri | A61M 3/0204 |
| | | | | 604/122 |
| 2004/0173019 | A1* | 9/2004 | McMillan | G01F 1/688 |
| | | | | 73/204.16 |
| 2011/0118705 | A1* | 5/2011 | Dekker | A61M 5/16886 |
| | | | | 604/890.1 |
| 2011/0308328 | A1* | 12/2011 | Haartsen | A61M 5/16886 |
| | | | | 73/861.41 |
| 2019/0184099 | A1* | 6/2019 | List | A61M 5/142 |
| 2019/0390990 | A1 | 12/2019 | Krywyj et al. | |
| 2020/0003646 | A1* | 1/2020 | Krywyj | G01F 1/666 |
| 2020/0061290 | A1 | 2/2020 | Thorvaldsen et al. | |
| 2021/0310840 | A1* | 10/2021 | Feagler | A61M 5/16886 |
| 2022/0377991 | A1* | 12/2022 | Sasaki | G01N 33/0098 |

FOREIGN PATENT DOCUMENTS

| | | |
|---|---|---|
| KR | 20070019383 A | 2/2007 |
| WO | 2018007502 A1 | 1/2018 |
| WO | 2020131557 A1 | 6/2020 |

OTHER PUBLICATIONS

Written Opinion (Form PCT/ISA/237) for International Application No. PCT/EP2022/058611 mailed Dec. 8, 2022 (8 pages).

* cited by examiner

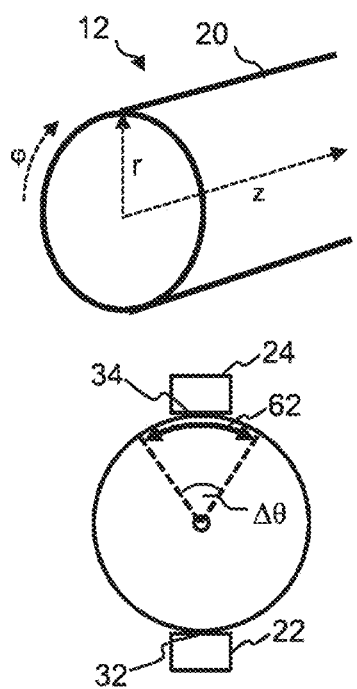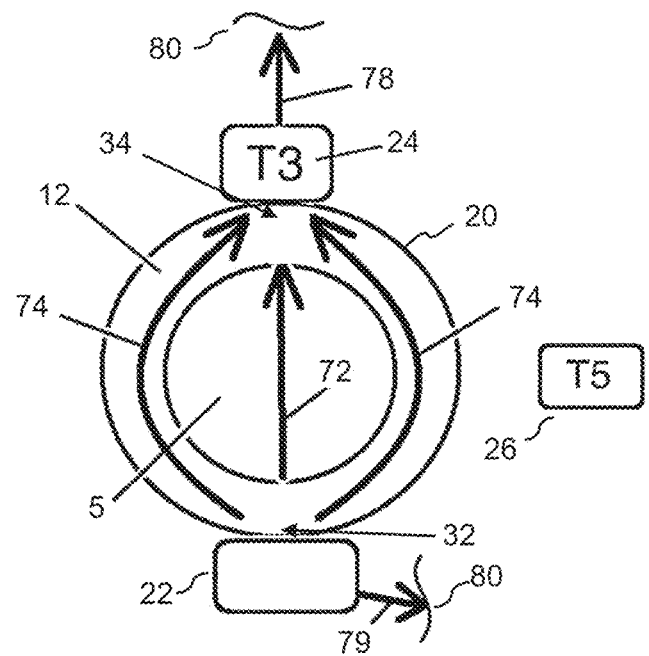
FIG. 7a
FIG. 7b
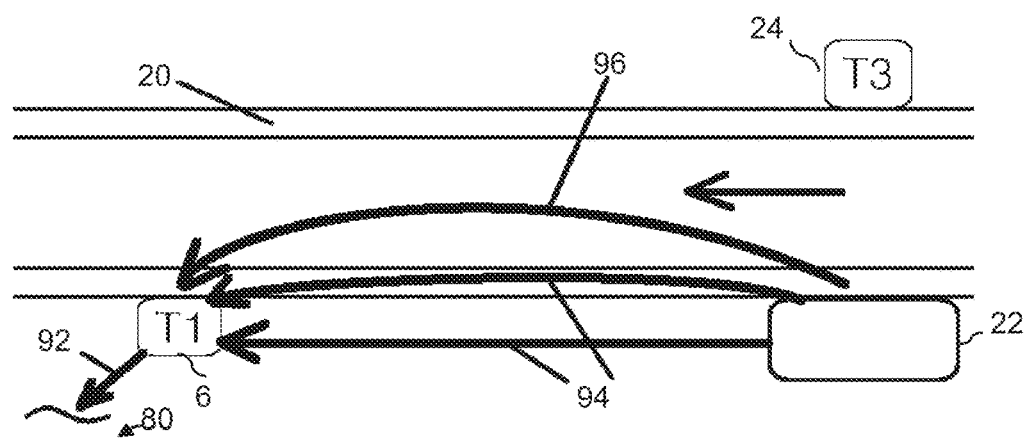
FIG. 8

FLOW SENSING DEVICE AND METHOD

CROSS-REFERENCE TO RELATED APPLICATIONS

This application is a continuation of International Application No. PCT/EP2022/058611 filed on Mar. 31, 2022, which claims priority to each of U.S. Provisional Patent Application No. 63/283,460 filed on Nov. 28, 2021 and to U.S. Provisional Patent Application No. 63/266,997 filed on Jan. 21, 2022, wherein the entire contents of the foregoing applications are hereby incorporated by reference herein.

FIELD OF THE INVENTION

The present application relates to a flow sensing device and method, in particular for use in sensing flow through an infusion or effusion line tubing.

BACKGROUND OF THE INVENTION

Plastic tubing lines are commonly used in medicine to infuse or flush liquids into or out of a patient. The flow of fluid in infusion tubing can be easily interrupted by a number of causes. Movement of the patient causing a disturbance of an intravenous (IV) needle at the infusion site can stop flow, as can an occlusion of the tubing caused by a kink. Transporting a patient connected to an IV bag may require that bag be taken down from a hanger during the transport, stopping IV flow. Flow can also be intentionally stopped during a procedure and then inadvertently kept off instead of being restarted when required. IV bags can run low or empty so infusion fluid no longer flows. Flow into arteries requires pressurizing the source fluid bag to overcome arterial pressure, and that pressure may become exhausted before the fluid bag is empty, causing flow to stop.

It is necessary to have a way to monitor flow in infusion tubing to make sure that it is flowing when it should be.

Traditionally, flow has been monitored by the use of a drip chamber which permits an observer to visually see fluid dropping in the chamber as an indication that there is flow in the tubing. There are also existing devices that clamp onto the drip chamber to optically observe the drops, such as the Drip Assist from Shift Labs or the Monidrop from Monidor. Alternatively, infusion pumps have means of detecting when fluid flow is blocked by measuring an increase in back-pressure if the tubing is occluded, or by optical or ultrasonic means.

In some situations it may be important to provide a warning if fluid flow has been stopped inadvertently, and the above methods of monitoring fluid flow have limitations.

One limitation is the cost and size of the above devices if they were to be used in a situation requiring only short-term monitoring (where a small disposable device may be the most appropriate), or in a mass casualty event where many such devices must be deployed at once, or where such a device must be carried in a crowded medic's bag and so must be small and light-weight. Transport situations in which there is vibration can result in difficulty monitoring flow using such existing devices because the vibration can affect the regularity of drops in a drip chamber.

There are situations where an infusion pump is not used, and instead simple gravity is used to flow liquids from a bag into the patient, or where a pressurized bag or vessel is used to source the liquids. In these cases, if a drip chamber is used it must be visually monitored to check that flow continues. However, this is not practical at night or in a dimly lit fluoroscopy theater, as the drops cannot be seen. This approach is also not feasible in the case that the drip chamber is not oriented vertically to allow drops to fall freely. It also requires inspection of the drip chamber at close range in order to see the drops, adding risk to nurses if the patient is infectious.

Sometimes, a very low flow rate, such as 5 ml per hour, is used just to keep open (TKO) a vascular access line should it be needed later to infuse drugs. TKO lines have very slow drop rates in a drip chamber, such as one drop per minute. Thus checking flow continuance in these cases is difficult; the drip chamber must be watched for a long time before any single drop will form and then fall off. The drip chamber may be overlooked if personnel are too busy with other things, such as during an emergency or in battlefield settings or mass evacuations where one medic is caring for many patients.

There are some settings where a drip chamber is not used at all, such as in blood donation centers, where, for example, the nurse can tell that flow is normal simply by monitoring the filling of the collection bag over time to see if it is progressing. Some ambulatory infusion systems such as the Baxter INFUSOR or INTERMATE systems use a pressurized vessel to propel the liquid and omit any drip chamber at all. In these cases, the only way to monitor flow is to observe emptying of the liquid in the pressure vessel over a long period of time.

It has further been recognized by the inventor that, in certain settings, such as military or emergency settings, the ambient light level may be too low to visually see the drops in a drip chamber, and keeping a drip chamber vertical so the drops fall properly is not always possible during emergency patient transport. In military settings in a combat zone, any device that emits light or sound is prohibited as it would give away the position of the soldier.

Thermally-based mass-flow sensors, properly designed, can overcome some of the above problems and are known to practitioners of the art. For example, DE 3827444 A1 describes a flow monitor for infusion lines that uses a heater element and two or three thermal sensors to determine occurrence of flow, flow rate and direction of flow.

However, known devices have slow responsiveness to detecting flow stopping or starting, and are mostly useful for measuring a quantitative flow rate of fluid. In some situations, such as when a device is needed to monitor the intentional stopping and starting of a fluid, it is particularly beneficial to detect and report the resumption of flow as quickly as possible to avoid giving unnecessary warning alarms.

Developments in this field would be of value.

SUMMARY OF THE INVENTION

The invention is defined by the claims.

According to examples in accordance with an aspect of the invention, there is provided a device for sensing a fluid flow through an infusion or effusion tubing line, comprising a housing adapted to removably couple to an outside wall of the tubing line, the housing accommodating a heating element and at least one temperature sensor. This may be referred to as a first temperature sensor or primary temperature sensor. The device further comprises a controller operatively coupled to the heating element and the first temperature sensor. The housing, when coupled to the tubing, is adapted to hold the heating element in contact with an outside wall of the tubing at a first contact area, and hold the first temperature sensor in contact with the outside wall of the tubing at a second contact area. The second contact area is substantially radially opposite the first contact area across the lumen of the tubing. In operation, the controller is adapted to simultaneously control the heating element to dissipate a (preferably substantially constant) heating power, and detect a flow parameter or condition based on an output from the first temperature sensor.

The controller may further generate an output indicative of the detected flow parameter or condition, for example a user-perceptible output or an electronic data output.

Thus, embodiments of the present invention propose provision of a temperature sensor substantially radially/ diametrically opposite the heater. In known thermal mass flow sensors for infusion lines, temperature sensors need to be provided upstream and downstream of the heater in order to detect speed and direction of flow. However, a problem with these known devices is that there is a high latency time between actual flow start and detection of flow start. By providing a sensor at this novel location, radially opposite the heater, rather than axially up/downstream from it, the thermal path between the heater and sensor is reduced, meaning that flow start can be sensed with a much shorter latency time.

Furthermore, the same effect cannot simply be achieved by moving an upstream or downstream sensor closer to the heater, for at least two reasons. First, if an up/downstream sensor is moved so that the axial distance between the heater and sensor matches the diameter distance across the tube, then the axial thermal path through the wall of the tubing is also commensurately reduced in distance. This leads to high thermal interference (heat directly travelling along the tube wall to the sensor without going through the fluid), which affects results because that interfering heat will obscure desired changes to the sensor by flow start/stop. By contrast, with a radially opposed sensor, the interfering thermal path directly through the tubing wall is longer than the thermal path through the fluid so that the fluid thermal path dominates the response of the sensor. Second, it is not just the thermal path length between sensor and heater which is significant, but also the total volume of fluid present between the heater and the sensor. With thermal mass based measurement, detected temperature changes rely on the heating of the whole volume of fluid present between the heater and the sensor. With a sensor axially displaced from the heater, the whole cylindrical volume of fluid between the heater and sensor must be heated before the sensor will detect the temperature change. By contrast, with a radially opposed heater, only the smaller volume of fluid extending radially between the heater and sensor needs to be heated. As a consequence, this further reduces time latency in detection of flow start. The optional compression of the tubing (discussed below) may further reduce the volume of fluid in the thermal path between the heater and the temperature sensor, making the system even more sensitive to flow changes at very low volumetric flow rates.

Another reason the same effect cannot be achieved by simply moving a downstream sensor closer to the heater can be explained as follows. The temperature, as sensed at the radially opposite position, goes up when flow stops as the heater warms the fluid and that warmth crosses the tubing diameter by thermal conduction through the fluid. Temperature falls when flow resumes as fresh cooler fluid replaces the warmer fluid interposed between the heater and temperature sensor. The signal polarity is in the opposite direction for prior art devices that have a temperature sensor downstream: those sensors warm up when flow occurs and they return down towards ambient temperature when flow stops and they are no longer influenced by warmed fluid. If one were to move a downstream sensor closer to the heater, at some point the signal polarity becomes indeterminate as it will end up with a response with characteristics of both a downstream and an opposed sensor: fluid that is stagnant will be heated, that heat will spread out from the heater and some of that heat will reach a downstream sensor if it is right next to the heater.

The temperature modulation at the radially opposite location is an order of magnitude greater than at downstream locations, resulting in a much larger signal per unit of heater power. This larger signal and power efficiency allows for a much lower heater power, so battery power becomes a viable option as it can now run for hours. Experiments show that a temperature sensor radially across the tubing from the heater had 12 times the temperature response than a downstream sensor.

It is noted that although reference is made to a first and second contact area, at minimum all that is needed is that the heating element and temperature sensor make contact at respective points of the tubing wall which are substantially radially opposite. Thus, throughout this disclosure, reference to contact areas can be replaced equivalently with reference to contact points without loss of functionality.

In this disclosure, by 'radially' is meant along a radial dimension of the tubing, meaning a dimension from one point of a boundary wall of the tubing to an opposite point of the boundary wall of the tubing. Radially opposite in this context means the same as diametrically opposite.

The tubing line may be understood as having an axial/ longitudinal dimension, along a direction of fluid flow through the tubing, and radial and circumferential dimensions orthogonal to the axial dimension.

The first contact area and second contact area may be substantially axially aligned. In other words, both contact areas are aligned at a same axial location along the length of the tubing. In other words, there is substantially no axial displacement between the position of the first contact area and the position of the second contact area.

As noted above, first contact area and second contact area are substantially radially opposed. Substantially radially opposite may mean for example radially opposite plus or minus some tolerance, for example, +/−5-10 degrees, i.e. the second contact area is positioned within an arcuate section of the tubing wall, the arcuate section having its center radially opposite the first contact area, and subtended by an angle at the center of the tubing (the tubing axial axis) of 5-10 degrees.

Driving the heating element with a substantially constant heating power means a substantially constant heating power over time, e.g. over a duration of an operation session of the device. Substantially constant power means a substantially constant power level; in other words substantially uniform power; in other words substantially invariant power. The advantage of using a substantially constant heating power, as opposed to a constant heater temperature, is that in the former situation the temperature of the heater will rise a fixed increment above the ambient temperature based upon the amount of power being dissipated. In this device, changes in flow affect the difference in temperature between the heater and the temperature sensor, so having the heater temperature track any ambient temperature changes with a fixed temperature offset will tend to compensate for variation in ambient temperature. In an extreme example, used to illustrate this concept only, if a fixed temperature heater were used (as opposed to fixed power) and the ambient temperature were to rise to the temperature of the heater, the temperature sensor would lose all sensitivity to flow because the heater would no longer be putting energy into the fluid. In this scenario, if instead fixed power is used, the heater temperature would just rise as the ambient temperature rises, and the temperature sensor would still be responsive to changes in fluid flow. Thus a constant power heater needs to only raise the fluid temperature a few degrees above whatever the ambient temperature is, whereas a constant temperature heater must always operate at a temperature substantially above the highest ambient temperature anticipated, and thus consume much more battery energy.

Substantially constant heating power means for example constant heating power +/−5%, more preferably +/−3%, even more preferably +/−1%.

Substantially constant may mean for example a constant time-average power, for example over a pre-defined moving average window. Substantially constant may mean for example a constant baseline power, for example with some fluctuation thereabout.

The controller may control the heating element to dissipate a substantially constant total thermal output power. Assuming that the heating element has a near 100% efficiency, then the total electrical input power to the heater can be assumed to be all converted to heating power. In this case, controlling the heating element to dissipate a substantially constant heating power simply means supplying/driving the heating element with a substantially constant electrical input power.

Detecting the fluid flow parameter or condition may be based on sensing variations in an output from the (first) temperature sensor while the heating element is being controlled.

The controller could be provided by circuitry, by one or more microprocessors, or by a combination of both. Circuitry of the controller may be distributed, so that the controller is not formed by a single integral unit. The controller in this case may be understood as a control means or control arrangement.

In some embodiments, the device further may further include a second temperature sensor, and wherein, when the housing is coupled to the tubing, the second temperature sensor is positioned for sensing either: an ambient temperature of the air in the environment of the device, or a temperature of the fluid at a location upstream from the heating element, and preferably at a location substantially uninfluenced by the thermal output of the heating element. If the second temperature sensor is for sensing an ambient temperature of the air in the environment, it may be spaced from the wall of the tubing in some cases, i.e. not in contact with the wall. If the second temperature sensor is for sensing the temperature of the fluid upstream from the heating element, it may be positioned to make contact with a point/area of the wall of the tubing at a location axially displaced from the axial location of the first temperature sensor and the heating element.

The controller may be adapted to detect the flow parameter or condition based on outputs of both the first temperature sensor and the second temperature sensor, based on compensating the temperature change measurement of the first temperature sensor using temperature change measurements of the second temperature sensor.

In other words, the second temperature sensor is used as a baseline temperature, and temperature change measurements detected at the second temperature sensor are offset or calibrated against temperature change measurements of the baseline second temperature sensor. In particular, a temperature change at the first temperature sensor, applied against the tube, reflects both changes in the ambient and changes in the flow, since both will alter the measured temperature. Only the flow-induced temperature changes are desired for the device. Therefore providing a second temperature sensor which is positioned so as to be only sensitive to the ambient temperature changes, or changes in the inlet temperature level of the fluid (where the inlet means the point of inflow into the section of the tubing retained by the housing), can be of benefit as the temperature change readings at the first temperature sensor can be offset or compensated using temperature change readings at the second temperature sensor readings. The resulting compensated temperature reading is reflective of substantially only flow-related temperature modifications.

The compensation of the temperature change measurement may be achieved by a resistor divider circuit in some embodiments, wherein both temperature sensors are thermistors and the first temperature sensor and second temperature sensor are arranged in a resistor divider arrangement, and the voltage output from the resistor divider arrangement is used to determine the flow parameter or condition. For example, the controller detects changes in the output from the resistor divider arrangement. A change in level or a change in slope may be taken as indicative of a change in flow stop/start condition for example.

In some embodiments, the device may further comprise a local power source, for example a battery, for electrically powering the heating element. This allows for providing a standalone device without a need for connection to an external power source. The device may be provided without the power source actually included in the device. For example, the device may simply comprise an electrical connection site adapted to connect with a local power source such as a battery. There may be a means for mechanically retaining the local power source within or attached to the housing during operation, while the power source is connected to said electrical connection site.

In some embodiments, the controlling of the heating element to dissipate a constant heating power comprises driving the heating element with a substantially constant power supply (i.e. constant input power to the heating element over time). Substantially constant power supply means a substantially constant power level, i.e. substantially uniform power or substantially invariant power level. Substantially constant power may mean for example constant power +/−5%, more preferably +/−3%, even more preferably +/−1%. Substantially constant may mean for example a constant time-average power, for example over a pre-defined moving average window. Substantially constant may mean for example a constant baseline power, for example with some fluctuation thereabout.

In some embodiments, the device comprises a local power source, and wherein the controller is adapted to convert an electrical output from the local power source into a pulse width modulated (PWM) electrical supply for driving the heating element, and to provide the pulse width modulated electrical supply to the heating element. The controller may be adapted to adjust a duty cycle of the PWM electrical supply in dependence upon the voltage of the power source so as to maintain a (substantially) constant power dissipation in the heating element. Maintaining a constant power dissipation by the heating element means for example maintaining a substantially constant (substantially uniform) power supply to the heating element. As a battery drains, its output voltage decreases. If the heating element is a resistor, where its power dissipation is the voltage squared divided by the resistance value, a decreasing voltage results in a decreasing power. Therefore, in such a circumstance, in order to maintain a constant power level to the heating element, an adjustment to the power output from the power source can be performed so as to keep the power level to the heating element constant. A pulse width modulation scheme is a simple and efficient means of achieving this. As the voltage drops, the controller can increase the duty cycle (the high/ON phase of the duty cycle) so as to compensate for the drop in voltage and thereby compensate for the corresponding drop in power, and thus maintain a substantially constant input power supply to the heating element.

The constant power input to the heating element may be a power level which is lower than the maximum power output possible from the battery when fully charged. In this way, the power level is kept lower from the start (by modulating the duty cycle), which provides the scope to maintain this lower power, even as the voltage output from the battery drops. For example, a typical supply power to the heating element may be less than one watt.

As noted above, the controller is adapted to detect a flow parameter or condition. In some embodiments, the detected flow parameter or condition is a flow stop/start condition. This means a binary detection of whether flow has stopped or started. This may be a flow stop/start event detection (i.e. detection of flow starting or stopping), and/or may be a flow status detection (i.e. continuous detection of whether flow is zero or non-zero). The detection may be based at least in part on sensing variations in an output from the (first) temperature sensor while the heating element is being controlled. In the specific embodiments where a second temperature sensor is used for compensating measurement of the first temperature sensor (see discussion above), then the detection may be based on sensing variations in an output from the first temperature sensor and the second temperature sensor while the heating element is being controlled. The variations in the first temperature sensor may be compensated according to detected variations in the second temperature sensor.

The device may use a thermal mass flow technique to detect flow stop/start.

For example, if the radially opposed (first) temperature sensor measures a rise in temperature above a baseline value or above a threshold value or faster than a certain slope, the controller detects that flow has stopped. If the (first) temperature sensor measures a fall in temperature by more than a certain amount or by more than a certain rate, the controller detects that flow has started.

In some embodiments, the controller may be adapted to generate an alert signal after a pre-set non-zero time delay following detecting flow stopping, and to terminate the alert signal immediately responsive to detecting flow starting. The alert signal may be a user perceptible alert signal, e.g. a sensory output such as an audible alarm, one or more visual indicators such as light indicators, or any other sensory output. The alert signal may be an electronic alert signal.

As will be discussed in more detail to follow, it is a realization of the inventor that, in actual clinical practice, it is most useful to generate an alert only after a certain time delay following detection of flow stopping. In particular, it is normal in some procedures for there to be multiple infusion lines into a patient simultaneously, each at a different vascular access port. During the procedure, the clinician selectively turns certain infusions off and then back on as different tools are repeatedly introduced and then removed. If one of the infusions is turned off for more than e.g. 1 minute there is a serious risk to the patient of blood clot formation and stroke. With the various different tubing lines being turned off and then on, it is easy for the doctor to lose track of which lines are stopped and for how long. If a device is configured to provide a flow alarm that sounds immediately upon flow stoppage, this simply adds to the workflow clutter since flow stoppage in a line is intentional so long as it lasts no longer than 1 minute. What is more valuable clinically is a device that sounds after a time delay of a duration which corresponds to the maximum time delay before there is risk to the patient. The alarm should then switch off immediately once flow restarts. This is more in accordance with clinical preference.

In some embodiments, the device may include means for applying a compression to the tubing wall when the housing is coupled to the tubing, wherein the compression reduces a radial distance between the first contact area and the second contact area. Radial here means relative to the radial dimension of the tubing. Thus the compression reduces the radial distance between the first contact area and second contact area across the lumen of the tubing. For example, the compression squashes or partially flattens (i.e. deforms) the tubing at the axial location of the heater and (first) temperature sensor, so that the heater and (first) temperature sensor are brought (radially) closer together. This shortens the radial thermal path length and fluid volume between the (first) temperature sensor and the heating element, which increases the sensitivity to flow stop/start.

In some examples, the means for applying a compression is adapted such that coupling the housing to the tubing has the effect of causing the compression to be applied.

In particular examples, the means for applying a compression is provided by the housing, wherein the housing is structured such that, when coupled to the tubing, the compression is applied by the housing to the tubing wall. In other words, in this example, when coupled to the tubing, a compression is applied by the housing to the tubing wall for reducing a radial distance between said first contact area of the heating element and said second contact area of the (first) temperature sensor. An alternative means for applying a compression might include an actuatable compression application means, e.g. electronically actuatable or manually actuatable. There may be for instance a squeezing mechanism which is actuatable to apply the compression. This might be actuated automatically upon coupling the housing to the tubing in some instances.

It is noted that in this disclosure, 'compression' of the tubing may mean applying a squeezing action or force to the tubing, with opposed application points on either side of the tubing.

In one particular set of embodiments, the housing may comprise first and second parts, e.g. hinged together, and the housing operable to couple to the tubing by moving the housing into a closed position with the tubing trapped between the first and second parts, and the housing structured to accommodate the tubing when so closed, and to hold the heating element and (first) temperature sensor at the first and second contact areas. In some cases, the first part may accommodate the heating element and the second part accommodate the (first) temperature sensor. A variety of other arrangements are also possible.

Due to the use of a radially opposed heating element and sensor, preferred embodiments can be configured so that the contact region between the device and the tubing is relatively short. This is because an upstream and downstream sensor is not required, and thus, contact with the tube is only needed at one axial location.

In some embodiments, the device may be configured such that, when coupled to the tubing, a respective axial section of the tubing wall either side of the first and second contact areas is not in contact with the device, for example exposed to the air.

In some embodiments, the housing may define an internal cavity or space within which an axial section of the tubing is received, and wherein the first contact area and second contact area are the only (or major) areas of contact between the device and the tubing inside the cavity or space. The remainder of the tubing may be exposed to an environment inside the cavity or space.

In some embodiments, the device may be configured such that, when coupled to the tubing, the first and second contact area form the only areas of contact between the device and the tubing (or, for example, at least of the axial section of the tubing which is received inside the housing).

It has been described above how using the first temperature sensor radially opposed to the heater can be used to determine if fluid flow has stopped or started. This sensor can be used to measure flow rate at very low flow rates, but it loses sensitivity as flow rate increases. In some embodiments, the device may include at least one further temperature sensor arranged, when the housing is coupled to the tubing, to be held against the outside wall of the tubing at a position axially/longitudinally displaced from the heating element along the length of the tubing (for example for sensing temperature either upstream or downstream of the heating element in operation), and wherein the controller is further operatively coupled with the at least one further temperature sensor, and wherein the controller is adapted to determine a flow rate and/or direction using the first temperature sensor and the further temperature sensor. If the one further temperature sensor is located downstream from the heater during normal forward flow, and flow restarts after being stopped, the reported temperature at the one further temperature sensor will rise as the reported temperature at the first temperature sensor falls, due to the volume of warmed fluid moving downstream away from the heater towards the new sensor. If that one further temperature sensor is kept at that position on the tubing, and flow had been stopped but then starts in the reverse direction, its reported temperature will not rise as the reported temperature at the first temperature sensor falls. In this way adding at least one further temperature sensor can determine the direction of flow. The flow rate can be inferred from the magnitude of the reported temperature change from the one further temperature sensor placed downstream, at the time when the first temperature sensor indicates that flow is occurring.

In preferred embodiments, the housing is adapted for coupling to an infusion or effusion line tubing having an outside diameter between 3 mm and 10 mm.

In some embodiments, the housing is adapted to permit coupling to tubing of a range of different outside diameters, for example between 3 mm and 10 mm.

In preferred embodiments, the device is a standalone device.

A further aspect of the invention provides a system comprising an infusion or effusion tubing line and a device in accordance with any of the embodiments or examples in this disclosure, the housing of the device coupled to the infusion or effusion tubing line.

A further aspect of the invention provides a kit of parts comprising an infusion or effusion tubing line and a device in accordance with any of the embodiments or examples in this disclosure.

A further aspect of the invention provides a method for sensing fluid flow through an infusion or effusion tubing line. The method comprises the following steps: holding a heating element in contact with an outside wall of the tubing at a first contact area; simultaneously holding a (first or primary) temperature sensor in contact with the outside wall of the tubing at a second contact area, wherein the second contact area is substantially radially opposite the first contact area across the lumen of the tubing; controlling the heating element such that it dissipates a substantially constant heating power; sensing a temperature output from the (first or primary) temperature sensor while the heating element is active; detecting a flow parameter or condition of fluid in the tubing based on an output from the (first or primary) temperature sensor.

In some embodiments, the method may further comprise compressing or squeezing the tubing at the location of the heater and (first) temperature sensor so as to reduce a radial distance between the first contact area and second contact area. The compression or squeezing is to deform the tubing to thereby reduce the thermal path length through the tubing at the location of the compression for the duration that the compression is applied.

In some embodiments, the force applied to compress the tubing may simultaneously act to hold the (first) temperature sensor and heater in contact with the tubing at the first and second contact areas.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 6b is a cross-sectional illustration of a housing according to the example device of FIG. 6a;

FIG. 7a illustrates the dimensions of the tubing and illustrates a tolerance range for positioning of the radially opposed temperature sensor;

FIG. 7b shows a layout of heating element and temperature sensor according to one or more embodiments, and further shows paths of heat flow from the heating element to the temperature sensor;

FIG. 8 shows, as a comparison with FIG. 7*b*, paths of heat flow longitudinally from the heater through the fluid to a hypothetical temperature sensor downstream from the heater;

DETAILED DESCRIPTION OF THE EMBODIMENTS

Figure 1:
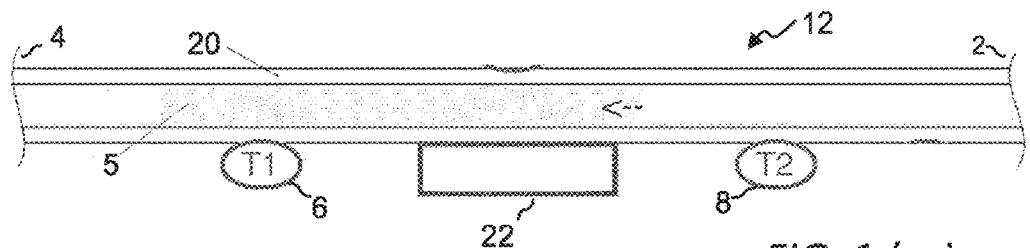
FIG. 1 shows a layout of a heater and temperature sensor in a prior art device.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

It is to be understood that when used in this specification, the terms intra-venous tubing, IV tubing, intra-arterial tubing, infusion tubing, effusion tubing, line or tubing all refer to the same thing, and can be any tubing that is intended to transport material into the body or out of the body or not related to a body at all. The term body refers to a human or animal body corpus.

Embodiments of the invention provide a device and method of action for a device that abuts the outside of infusion or effusion tubing and uses thermal mass-flow techniques to determine if fluid is flowing or stopped within the tubing. The device includes a housing which carries a heater and temperature sensor arranged such that, when the housing is coupled to the tubing, the heater and temperature sensor are at opposite sides of the tubing wall, in facing relationship. They are for example approximately diametrically opposed.

Optionally, in some embodiments, if fluid flow is detected to have stopped, the device will alert the operator after a specifically defined delay time, and if fluid subsequently restarts flowing, the alert is terminated promptly, e.g. approximately instantly.

Optionally, in some embodiments, there is applied an intentional distortion of the flexible tubing to reduce the diametric distance between the heater and the temperature sensor, to optimize the function.

Techniques are further described in accordance with some embodiments to address issues arising from battery operation, from changes in ambient temperature and from the presence of interfering fluids and drips.

By way of introduction, it is a motivation behind at least some embodiments of the present invention to improve upon known methods of monitoring fluid flow in infusion tubing (some of which have been discussed above) by providing a relatively small, very low-cost device that can easily clip onto IV tubing to monitor fluid flow, and that does not actually touch the infusate directly, and thus does not need to be sterile.

In preferred examples, this device may give an alert if fluid flow stops for longer than a predetermined length of time. The alert could either be visible, audible, a silent mechanical indicator, by wired or wireless electronic communication or some combination of these. The alert would clear immediately upon resumption of fluid flow.

To be most universally useful, in some embodiments, the device is configured such that it is operable with different types (e.g. shapes) and diameters of infusion or effusion tubing. For example, this could include suitability for use with high-pressure tubing used for arterial infusions, which are less than optically clear due to a reinforcing braid in the tubing wall. Typically, infusion tubing outer diameters range from 3.6 mm to 5.7 mm. Thus, by way of example, some embodiments provide a device which is operable to fit to tubing of any diameter between about 3 mm and about 6 mm.

It would also be of advantage for a device to be operable with a variety of fluids, including opaque liquids such as blood or suspensions. It would also be of advantage for a device to be operable in any position or orientation with respect to gravity, even in Space with no gravity, be insensitive to vibration during transport, and be battery powered to operate for several hours while in the field.

The above represent a range of advantageous features and effects, which are not essential to the inventive concept, and some, all or none of which may be features of embodiments of the present invention.

By way of explanatory background, FIG. 1 shows an example arrangement of a heater 22, and first 6 (T1) and second 8 (T2) temperature sensor of a known flow sensing device. The heater and temperature sensors are all arranged in contact with an outer tubular wall 20 of an infusion or effusion line tubing 12. FIG. 1 shows an inlet 2 and outlet 4 to the section of tubing which is illustrated. A fluid flows through the lumen 5 of the tubing along the direction indicated by the arrow. Temperature readings from the upstream and downstream sensors can be compared so as to derive a fluid flow direction and rate. An example device which uses this configuration is described in DE 3827444 A1 for example.

Figure 2:
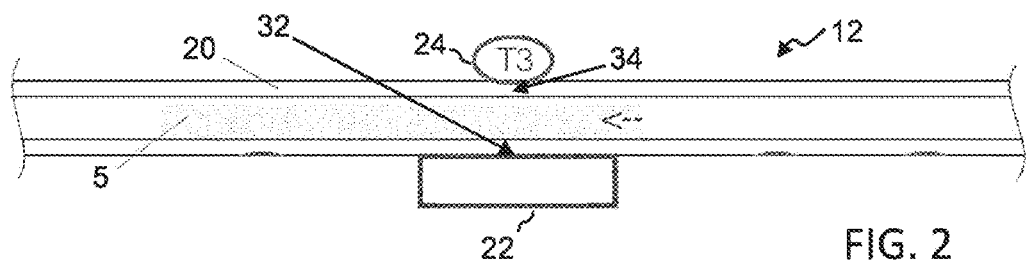
FIG. 2 shows a layout of a heater element and temperature sensor according to one or more embodiments of the invention, wherein the heater element abuts the outside of the IV tubing, and a temperature sensor is directly across the tubing from the heater and abuts the tubing.

FIG. 2 schematically illustrates a layout of components in accordance with one or more embodiments of the present invention. The device comprises a single temperature sensor 24 (T3) held against the tubing wall 20 at a contact area 34 substantially radially opposite the contact area 32 of the heater to the tubing wall. The temperature sensor is labelled T3 to contrast it with the prior art arrangement comprising sensors T1 and T2, which are absent in the particular arrangement shown in FIG. 2. As will be explained later, this arrangement permits detection of flow start and stop with significantly reduced latency compared to the arrangement of FIG. 1 due to the shorter thermal path between the heater and temperature sensor.

Figure 5:
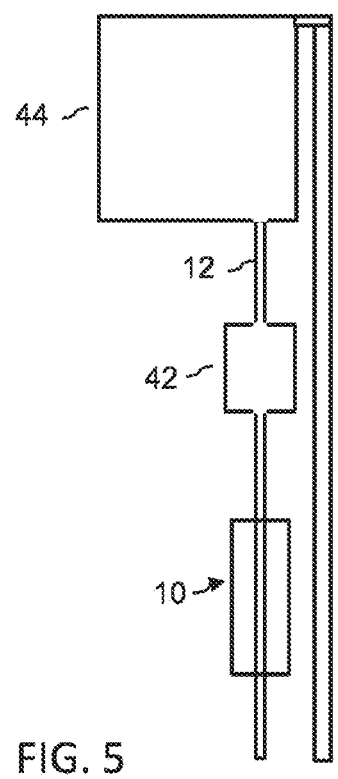
FIG. 5 shows an example flow sensing device in operation, coupled to an IV line tubing.

In more detail, in accordance with one or more embodiments, and with reference also to FIG. 5 and FIG. 6, there is provided a device 10 for sensing a fluid flow through an infusion or effusion tubing line 12. The device comprises a housing 14 (see for example FIG. 6) adapted to removably couple to an outside wall 20 of the tubing. The housing accommodates a heating element 22 and at least one temperature sensor 24, T3. The device further comprises a controller (not shown) operatively coupled to the heating element 22 and temperature sensor 24, T3. The at least one temperature sensor, T3, may be referred to as a first temperature sensor or primary temperature sensor.

The housing 14 when coupled to the tubing, is adapted to hold the heating element 22 in contact with an outside wall 20 of the tubing 12 at a first contact area 32, and hold the (first) temperature sensor 24, T3 in contact with the outside wall of the tubing at a second contact area 34. The second contact area 34 is substantially radially/diametrically opposite the first contact area 32 across the lumen 5 of the tubing.

In operation, the controller is adapted to simultaneously: control the heating element 22 to dissipate a substantially constant output heating power (for example by controlling electrical supply to the heating element of a substantially constant input power); and detect a flow parameter or condition of the fluid flow based on an output from the temperature sensor 24, T3.

The temperature sensors can be standard sensors familiar to someone skilled in the art, including but not limited to thermistors, silicon sensors and resistance-temperature detectors (RTDs).

This invention will operate in total darkness, will operate in any physical orientation with respect to gravity, may be small, very low cost, lightweight and may be battery powered so it is self-contained. It may work on a variety of fluids including saline, water, electrolyte solutions, blood, blood products, blood expanders, urine and liquid medications, either in solution or in suspension.

Figure 3:
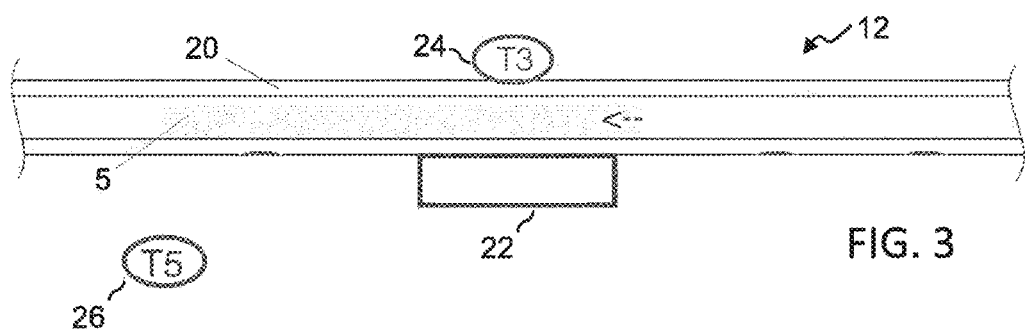
FIG. 3 shows a layout of heating element and temperature sensors according to a further one or more embodiments.

As will be described in more detail later, and as schematically illustrated in FIG. 3, in some embodiments, a further temperature sensor 26 (labelled T5 in FIG. 3) may be provided which is arranged either for sensing an ambient temperature or for sensing a temperature of the fluid upstream from the heater.

In more detail, in accordance with some embodiments, the device further includes a second temperature sensor 26, T5 and, when the housing 14 is coupled to the tubing, the second temperature sensor is positioned for sensing either: an ambient temperature of the air in the environment of the device, or a temperature of the fluid at a location upstream from the heating element, preferably at a location substantially uninfluenced by the thermal output of the heating element. In these embodiments, the controller may be adapted to detect the flow condition or parameter based on outputs of both the first temperature sensor 24, T3 and the second temperature sensor 26, T5, based on compensating the temperature change measurement of the first temperature 24, T3 sensor using temperature change measurements of the second temperature sensor 26. T5. This is described in more detail later.

Figure 4:
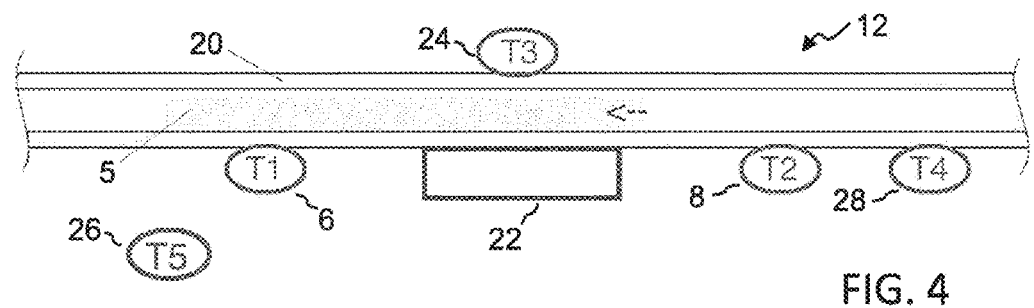
FIG. 4 shows a layout of heating element and temperature sensors according to a further one or more embodiments, wherein three temperature sensors are included touching the IV tubing, one downstream and two upstream from the heating element and one ambient temperature sensor.

As schematically illustrated in FIG. 4, in accordance with some embodiments, there may additionally be provided at least one further temperature sensor arranged for sensing a temperature of the fluid at a location upstream and/or downstream of the heating element 22. For example, as illustrated in FIG. 4, a downstream temperature sensor 6, T1 similar to that shown in FIG. 1 could be provided. Additionally or alternatively, an upstream temperature sensor 8, T2 similar to that shown in FIG. 1 could be provided. Additionally or alternatively, a further temperature sensor 28, T4 could be provided for sensing a temperature of the fluid close to an outlet of the infusion or effusion fluid source, for use in calibrating temperature measurements. This will be described in greater detail to follow. The at least one further temperature sensor 6, 8, 28 may be arranged, when the housing is coupled to the tubing, to be held against the outside wall of the tubing at a position either upstream or downstream of the heating element, and wherein the controller is further operatively coupled with the at least one further temperature sensor, and wherein the controller is adapted to determine a flow rate and/or direction using the first temperature sensor and the at least one further temperature sensor.

FIG. 5 illustrates the device 10 in accordance with an embodiment in situ, coupled to an infusion line tubing 12. An IV bag 44, containing liquid, is shown hanging from a pole. The IV tubing 12 drains the bag into a drip chamber 42 which is shown below the bag. The drip chamber allows visual determination of the amount of flow in the tubing by counting the rate at which drops of known volume are released into the chamber. The device is shown removably coupled, e.g. clipped, to the tubing at a position downstream from the drip chamber, e.g. directly below the drip chamber.

The device 10 can be provided as a standalone unit. The device touches the outside of tubing, such as infusion tubing, and will monitor the presence of flow of a liquid fluid within that tubing, for example detecting when liquid fluid flow is stopped for a period of time, or when liquid fluid flow has been restarted.

Figure 6A:
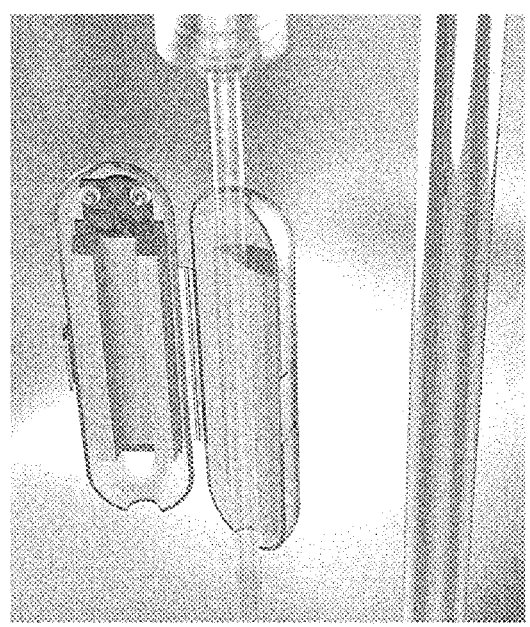
FIG. 6a is a perspective view CAD rendering of a housing of an example device according to one or more embodiments, with the housing being open prior to being clipped onto IV tubing.
Figure 6B:
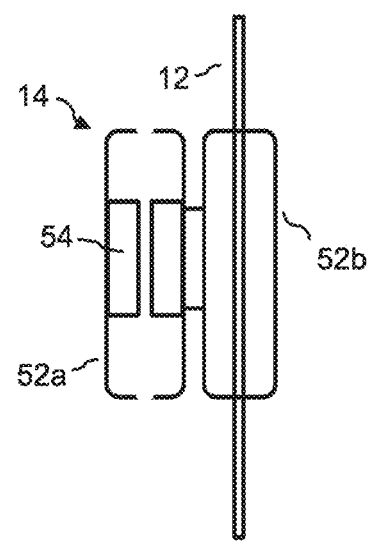

FIGS. 6a and 6b further illustrate a design of an example housing in accordance with a particular embodiment. FIG. 6 shows the device opened up prior to being clipped onto the outside of the IV tubing. FIG. 6a shows a 3D CAD drawing of the example housing. FIG. 6b shows a cross-section through the housing.

In the illustrated example, the housing 14 comprises first 52a and second 52b parts hinged together. As illustrated, the housing is adapted to accommodate the tubing running through it. By way of one possible example, the first part 52a may accommodate the heating element 22 and the second part 52b may accommodate the temperature sensor 24, T3, and the housing may be operable to couple to the tubing by hinging the housing into a closed position with the tubing 12 trapped between the first 52a and second 52b parts, and the housing structured to accommodate the tubing when so closed, and to hold the heating element and temperature sensor at the first and second contact areas. In other examples, both the heating element 22 and temperature sensor 24, T3 could be accommodated in a same half of the housing. This arrangement permits easily clipping onto IV tubing as shown in FIG. 6 and does not touch the fluid inside the tubing, thus does not need to be sterile. This device can be easily unclipped and removed from the IV tubing.

The principles behind the detection of flow using embodiments of the present invention will now be briefly outlined.

The flow sensing device 10 according to embodiments of the invention can be used to detect whether fluid is flowing inside infusion tubing 12. By way of example, detection of flow start and flow stop (a flow start/stop condition) may be made. This may be useful for example in a device whose principal purpose is to sound an alarm if liquid fluid flow stops, for example for an excessive period of time, as described above. This sensing principle however is not restricted to such use. The sensing method could even be embedded as an OEM (original equipment manufacturer) component in another finished device, to monitor for flow of fluid in that device.

With reference to FIG. 7, the method of flow detection comprises using the surface heater element 22 to heat a small section (a first contact area 32) on one sidewall 20 of the infusion tubing 12 and to measure the temperature at a location 34 on the opposing sidewall of the tubing using the temperature sensor 24, T3. Using this method, at minimum, only one temperature sensor is required, labeled T3 in FIG. 7, and it is located substantially across the diameter of the tubing from the heater 22, for example directly radially across the tubing on the tubing wall opposite where the heater is located.

It is to be noted that when the words "opposite side" or "opposed" or "across" are used it is not required that the temperature sensor 24, T3 be located exactly at the point that is the farthest around the tubing from the heater; the temperature sensor should be substantially around the tubing from the heater but there is some latitude on how far around it must be.

For example, FIG. 7 (bottom left) schematically illustrates an example tolerance range for the location of the temperature sensor 24, T4 relative to the heater 22. Substantially radially opposite may mean for example radially opposite plus or minus some tolerance, for example, +/−5-10 degrees, i.e. the second contact area 34 is positioned within an arcuate section 62 of the tubing wall, the arcuate section 62 having its center radially opposite the first contact area 32, and subtended by an angle 40 at the center of the tubing (the tubing axial axis) of 5-10 degrees. Another example tolerance range for the positioning of the second contact area 34 might be defined by a circumferential section 62 of the tubing circumference, having its center radially opposite the heating element, and the length of the circumferential section being a defined percentage of the total circumference, for example less than 25%, preferably less than 20%, more preferably less than 10%, for example less than 5%.

As illustrated in FIG. 7 (top left), the tubing line 12 may be understood as having an axial dimension, z, along a direction of fluid flow through the tubing, and a radial, r, and circumferential, $\varphi$, dimension orthogonal to the axial dimension. The radial, r, and circumferential, $\varphi$, dimension define a radial plane perpendicular to the axial (longitudinal) axis, z, of the tubing.

The first contact area 32 and second contact area 34 may be substantially axially aligned. In other words, both contact areas are aligned at a same axial location along the length of the tubing 12. In other words, there is substantially no axial displacement between the position of the first contact area and the position of the second contact area.

The thermal resistance between the heating element 22 and temperature sensor T3 through the radial fluid path 72 when the fluid is not flowing should ideally be lower than the thermal resistance along the circumferential thermal path 74 through the tubing wall from the heater to sensor, and ideally is also lower than the thermal resistance along the path 78 from T3 to the ambient 80. This has the effect that a change in the thermal resistance through the radial fluid thermal path 72 has the greatest influence on sensor T3.

Based on a measured relationship between the temperature sensor 24, T3 signal and time, it is possible to determine whether fluid is flowing or has stopped.

For example, if the temperature at T3 starts to rise, then fluid flow in the tubing may be considered to be stopped, since the heater 22 is raising the temperature of the stagnant fluid. If the temperature at T3 starts to fall, then fluid flow in the tubing may be considered to have restarted since fresh cooler fluid is interposed between the heater 22 and temperature sensor 24, T3.

A novel feature of embodiments of the invention is that by positioning temperature sensor T3 substantially across the tubing from the heater 22, the signal T3 can be used to clear a flow alarm quickly when flow resumes because the thermal path 74 is immediately and profoundly interrupted even with a small amount of flow. Any liquid heated by the heater is swept downstream before its heat can reach sensor T3, so T3 promptly returns to the temperature of the incoming liquid. This (radially opposed) location of T3 results in the largest change in temperature as a function of flow of any possible location for a temperature sensor that touches the tubing, resulting in a large temperature signal, which in turn simplifies the connected electronic circuitry (to be discussed later).

Referring again to FIG. 7, as mentioned, this schematically shows paths of heat flow from the heating element 22 to the temperature sensor T3, through the walls of the tubing (path 74), through the fluid inside the tubing (path 72), from the temperature sensor T3 to ambient (path 78) and from the heater 22 to ambient 80 (path 79). FIG. 7 also shows an optional ambient temperature sensor 26, T5 (mentioned above) which does not touch the tubing.

As mentioned, if the infusion tubing 12 is heated at one point 32 on one side of the wall 20 of the tubing, and if a temperature sensor 24, T3 is placed radially across (e.g. directly radially across) the tubing from the heater 22, in contact with the wall 20 on the opposite side of the tubing 12, then it is possible to determine whether fluid is flowing in the tubing or whether fluid is not flowing based on the signal output from the temperature sensor as a function of time.

Prior art devices do not use this sensor location. This may be because prior art device have a primary focus on quantifying the flow rate, and this sensor location is less efficient for measuring rate of flow. However, for a binary flow/no-flow detection, the inventor has found that this is the best position for the sensor. This is for the following reasons.

First, the temperature modulation at this sensor location is an order of magnitude greater than at downstream locations, resulting in a much larger temperature change signal per unit of heater power. It is also noted that this larger signal and power efficiency allows for a much lower heater power, and therefore battery power becomes a viable option for powering the heater. For example, a typical power level of the heater might be in the order of 0.25 Watts. With such a power level, the heater can be run for hours on battery power. The experiments by the inventor has shown that a temperature sensor radially across the tubing from the heater had 12 times the temperature response to flow than a downstream sensor for a given unit of heater power.

Second, it is to be noted that the same effect cannot be achieved simply by moving a downstream temperature sensor closer to the heater 22. This can be understood for the following reasons.

The temperature at the substantially radially opposite location goes up when flow stops as the heater 22 warms the fluid and that warmth crosses the tubing diameter (along path 72) by thermal conduction. Temperature falls when flow resumes as fresh cooler fluid replaces the warmer fluid interposed between the heater 22 and temperature sensor 24, T3. By contrast, the signal polarity is in the opposite direction for prior art devices that have a temperature sensor downstream: the temperature downstream increases when flow occurs and returns back down towards ambient temperature when flow stops, since the temperature is no longer influenced by warmed fluid. As a result of this, it is not possible to achieve the same effect as embodiments of the present invention by simply moving a downstream sensor closer to the heater (i.e. to thereby reduce the thermal path length between the heater and the sensor). This is because, as the sensor were to move closer to the heater, at some point the signal polarity would become indeterminate, since the signal would show a response with characteristics of both a downstream and an opposed sensor. In particular, fluid that is stagnant will be heated, that heat would spread out sideways from the heater and influence the temperature of the downstream sensor if it is very close to the heater, thus interfering with the temperature change response due to flowing fluid.

Additionally, a downstream temperature sensor which is close to the heater would be more strongly influenced by stray, unintended thermal pathways directly between the heater and sensor through the wall 20 of the tubing. This is illustrated in FIG. 8 which shows paths of heat flow longitudinally from the heater 22 through the fluid (path 96) to a hypothetical sensor T1 downstream, from the heater to sensor T1 by paths other than through the fluid (paths 94) and from temperature sensor T1 to the ambient 80 (path 92). These stray thermal pathways will dominate the temperature sensor 6, T1 response if it is positioned next to the heater. So, in prior art devices, a downstream sensor must be positioned far enough away from the heater to avoid being warmed when fluid flow is stopped.

Another benefit of embodiments of this invention is compact size. In prior art devices using a downstream sensor, the sensor must be some minimum distance from the heater, for reasons already discussed. This increases the physical size of the whole device, since it must touch the tubing at two, separated axial locations along the tubing. If the sensor and heater touch the tubing at the same axial position along the tubing length, then the device can be made more compact. This allows it to be manufactured with lower cost and results in a device which is more portable and more useful in some applications.

In the particular case of detecting a binary flow start/stop condition, the radially opposed sensor location provides a much simpler signal response to start/stop of flow than a comparable downstream sensor arrangement. The thermal signal at a downstream temperature sensor depends upon the flow rate. While this makes it useful to quantitate the flow rate in prior art devices, thus variation in output with flow rate only adds an additional, unwanted variable uncertainty when seeking specifically to make a binary flow/no-flow detection. If the flow rate is slow, the downstream sensor temperature will rise, but if the flow rate is fast enough the signal downstream will actually decrease back towards ambient, because the heater will not have time to heat a unit of fluid before it sweeps past the heater. This is taught in DE3827444A1. US 2020/061290 A1 further refers to this inversion of the signal at high flow rates as a "turning point". By contrast, the sensor that is radially opposed to the heater quickly cools toward ambient temperature with the start of even a very small flow, and it stays cool as flow increases, thus leading to a large temperature signal response that is not very dependent upon flow rate.

Thermal interference through direct thermal conduction along the tubing wall is reduced for a device which touches the tube along only a limited length of the tubing. In particular, it is in general preferable to minimize extraneous contact with the tubing in order to minimize undesired stray thermal pathways that can interfere with the desired thermal path signals. A device with a temperature sensor axially displaced from the heater must be in contact with the device along a relatively extended section of the tubing. By contrast, a device in accordance with embodiments of this invention need only contact the tubing at a very restricted axial location.

As mentioned above, in accordance with some embodiments, an additional temperature sensor, T5, is provided which is arranged to sense a temperature of the environment or of the fluid upstream from the heater, for use in calibrating temperature change measurements at the location of the main temperature sensor T3.

The operation of the embodiment of FIG. 2 assumes that the heater 22 power is large enough to make the resulting heater surface temperature always stay well above any ambient temperature around the device, even if ambient temperature varies over a range. In this case, only a single temperature sensor T3 is needed to detect whether fluid is flowing or not, since the variation in signal with ambient temperature is a small proportion of the signal change with flow. Prior art devices that attempt to quantitate a flow rate always use multiple temperature sensors with their attendant increased complexity. But, especially in a battery powered device, there is an incentive to operate the heater at as low a power as possible in order to extend the battery life, so the heater temperature may only operate at a few degrees above the ambient temperature. However, the ambient temperature may vary, and its range may be greater than the temperature change induced in a fluid by the low power heater. In this situation, accuracy is improved by compensating the temperature sensor T3 reading for changes in ambient temperature. Using simply a fixed temperature threshold to detect whether fluid is flowing may not work if the ambient temperature variation is larger than the variation due to flow.

A second temperature sensor (discussed above as T5) may be introduced to facilitate this ambient temperature compensation. An example arrangement including an ambient temperature sensor T5 was shown in FIG. 3. The second temperature sensor may be accommodated in the housing.

If the temperature sensors report temperature directly in degrees, such as semiconductor sensors that output 10 mV/degree C. or semiconductor junctions that change −2 mV/degree C., then ambient temperature compensation can be achieved by simply taking the difference between two sensors T3 and T5 to derive a sensor difference signal, and making flow/no-flow detections based upon this difference signal (e.g. by looking for a change in the difference signal level or slope compared to a threshold).

Alternatively, often less expensive thermistor temperature sensors may be used which may change their resistance as a percent per degree C., rather a specific resistance per degree. Thus, if thermistors are used, these may be connected in ratio to compensate for ambient temperature. A simple voltage divider with one thermistor in the upper arm and one thermistor in the lower arm will achieve this, as ambient temperature change affects both sensors by the same percentage and thus the output voltage of the divider does not change as ambient temperature changes.

Of course, use of a microprocessor which can covert input sensor signals to equivalent numerical temperature signals is also possible, in which case a simple difference signal between the converted temperature signals of T3 and T5 could be computed and monitored to detect flow condition or parameters.

In one prototype, the compensation for ambient temperature was in fact achieved by using temperature sensor at the location of T1 (see FIG. 1 or FIG. 4), i.e. arranged touching the tubing downstream from the heater. T1 will respond thermally to flow rate in the opposite direction from T3: when there is fluid flow then T1 warms up as the warmed fluid flows downstream, at the same time as T3 cools down as new, cooler fluid is interposed between the heater and T3. Because the two sensors operate in opposite directions, one can use them in ratio to create the maximum signal modulation due to flow.

Figure 9A:
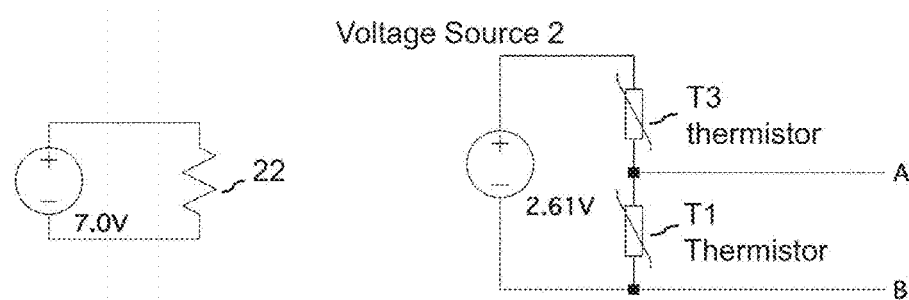
FIG. 9*a* shows example electrical connections used in a prototype for sensing flow based on temperature readings.

If the sensors are thermistors, where the resistance percentage change is proportional to temperature, then using a resistive divider gives both the largest temperature signal modulation and also automatically compensates for ambient temperature variation, since such variation changes the resistance of each thermistor by the same percentage, resulting in no change in voltage output with ambient temperature variation. An example circuit with a suitable resistive divider arrangement is shown in FIG. 9a (right). This shows an experimental sensor module that was constructed to test the invention, where T3 is a negative temperature coefficient (NTC) thermistor radially opposed to the heater and T1 is a NTC thermistor touching the tubing downstream from the heater. FIG. 9a (left) shows the heater as a resistor, for example of 200 ohms.

Figure 9B:
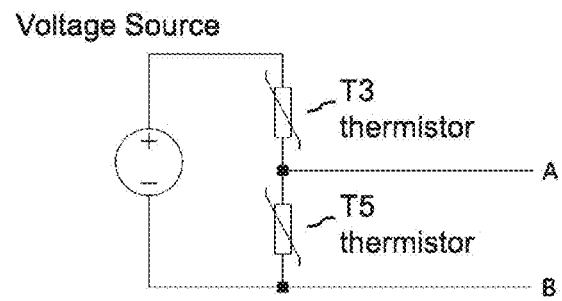
FIG. 9*b* shows an electrical topology for compensating for ambient temperature variation, using an ambient temperature sensor that is not touching the tubing.

FIG. 9b shows an electrical topology to inexpensively compensate for ambient temperature variation, using an ambient temperature sensor T5 that is not touching the tubing.

Illustrated voltages are exemplary only.

When the device compensates for variation in ambient temperature, the heating element 22 need, at minimum, only dissipate a fraction of one Watt of power (i.e. generate a heating power of less than 1 Watt) and the temperature change of the fluid induced by the heater need only be a few degrees or even a fraction of a degree. In experiments proving the concept of this invention, a heater power dissipation of 0.25 Watts was sufficient to provide a useful signal.

Figure 10:
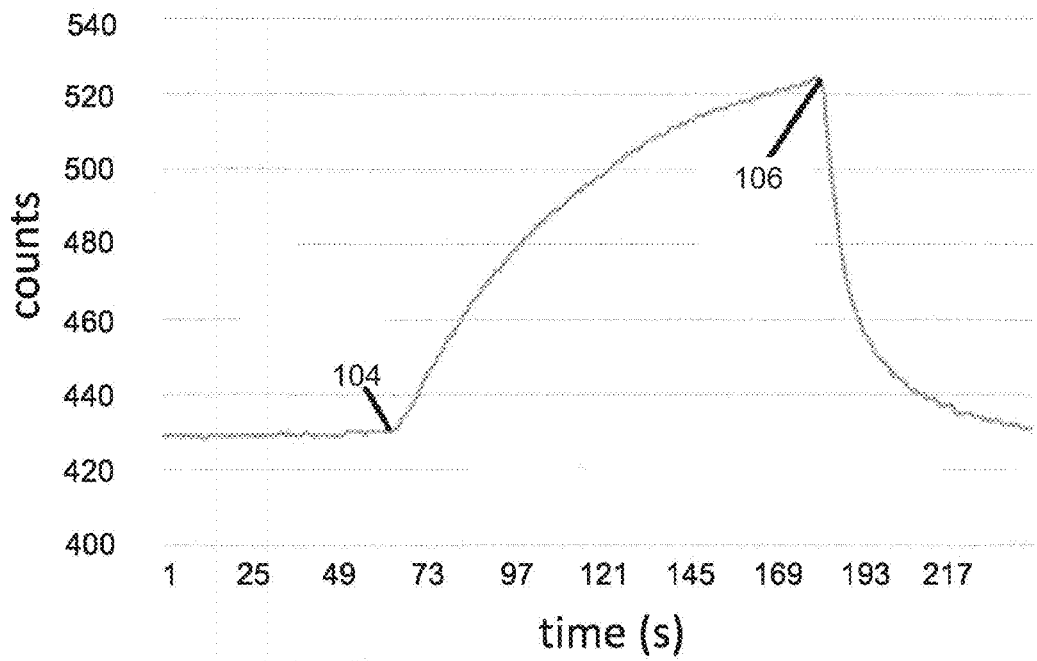
FIG. 10 shows the output of a thermistor resistive divider circuit in a prototype device when liquid fluid is flowing for the first 60 seconds, then it stops for 120 seconds, then it restarts flowing at 180 seconds.

FIG. 10 illustrates the output of a thermistor resistive divider circuit in a prototype device, with T3 as the upper resistor in the divider and T1 the lower resistor (see FIG. 9a (right)), when the heater is dissipating a constant heating power of 0.25 Watts. Water is the fluid. It flows for the first 60 seconds at about 200 milliliters/hour. It then stops for 120 seconds. It then restarts flowing at the 180 second point. The x-axis is time in seconds and the y-axis is counts out of a 10-bit analog-to-digital converter. The change when water is flowing versus not flowing is clearly visible. In particular, inflection point 104 indicates the point at which flow stops, and inflection point 106 indicates the point at which flow starts.

The measurements of the inventor demonstrate that the thermal signal at T3 due to changes in flow is an order of magnitude larger than the thermal signal downstream at T1 due to changes in flow. By the time the heat reaches the T1 location there is only a slight increase in temperature of T1 due to flow, whereas T3 is in close thermal proximity to the heater through path 72 (see FIG. 7). However, ambient temperature variation affects both sensors equally. Thus the advantage of including optional sensor T1 is primarily to compensate for ambient temperature, and only to a minor extent does it help determine if there is fluid flow.

Since the primary advantage to using optional sensor T1 is thus to compensate for ambient temperature variation when operating the heater at a lower power, in a preferable set of embodiments, a separate dedicated ambient temperature sensor T5 can be substituted for sensor T1 (see e.g. FIG. 3). T5 only measures ambient temperature and does not need to touch the tubing. A major advantage of this arrangement is that T5 can be remote from the tubing, which reduces thermal interference. Using T5, the same compensation for ambient temperature variation is achieved, at the cost of only a small reduction in signal modulation due to flow. The advantage of using a sensor T5 remote from the tubing is that the whole device can be made considerably smaller since the only required physical connection to the tubing is at a single axial point along the tubing with the heater 22 on one side and T3 on the other. This significantly reduces the size of the device as it does not need to also touch the tubing downstream. This also for example enables greater options for the location of the battery and electronic circuits with respect to the tubing. For example, FIGS. 23a and 23b (described later) shows that the whole device can be made only slightly larger than a one cell lithium AAA battery used to power it, and only touch the tubing at one point.

It is noted that in the above embodiment, the compensation is achieved by analog circuitry rather than by a microprocessor. Reference in this disclosure to a controller compensating the temperature output from sensor T3 should be understood as covering the option that the controller is a control assembly which includes the analog compensation circuitry.

Thus, at least some embodiments of the invention include an electrical circuit topology that automatically compensates for changes in ambient temperature and that simplifies the electronic design used to detect cessation or resumption of flow of liquid in the tubing.

Figure 11:
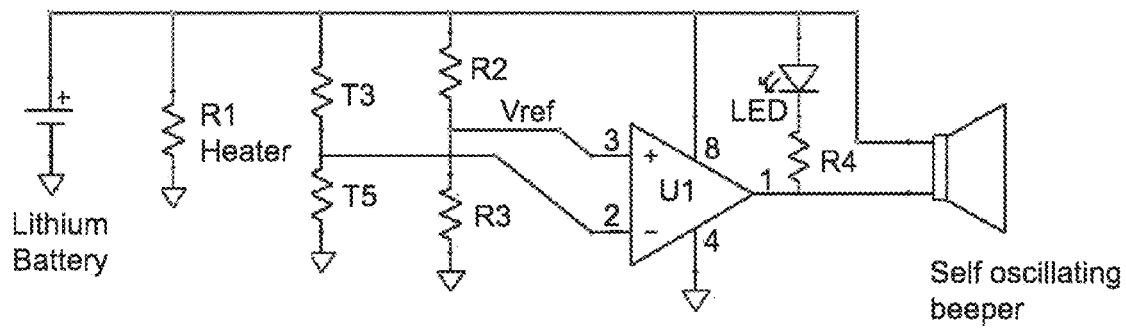
FIG. 11 shows a simple electronics topology that can be implemented at low cost.

FIG. 11 shows a very simple electrical circuit that reports a no-flow condition following the principals of one or more embodiments of this invention. Thermistor temperature sensors T3 and T5 are used in a resistive divider arrangement so compensation for ambient temperature is automatically achieved. In the illustrated example, these thermistors are each 1K Ohm at 25 degrees C., to resist ionic fluid contamination. If using a lithium battery, the voltage is approximately constant over much of its capacity discharge, so the power in the resistor heater element R1 is more constant than using an alkaline battery chemistry. Resistor divider R2 and R3 create a threshold voltage Vref above which the flow will be considered stopped, and that threshold automatically adjusts for the small voltage change in the battery voltage as it discharges. Electronic comparator U1, a red light emitting diode and a beeper alert when flow has stopped. This design relies on the natural thermal response time of the fluidics to provide the desired delay when reporting a stopped-flow condition, with some adjustment of this time being possible by changing the ratio of resistances R2 and R3. In this example, the controller previously discussed is provided by the circuit shown in FIG. 11.

The simplicity of this circuit means that it can be manufactured at very low cost, consistent with a disposable single-use device.

Figure 12:
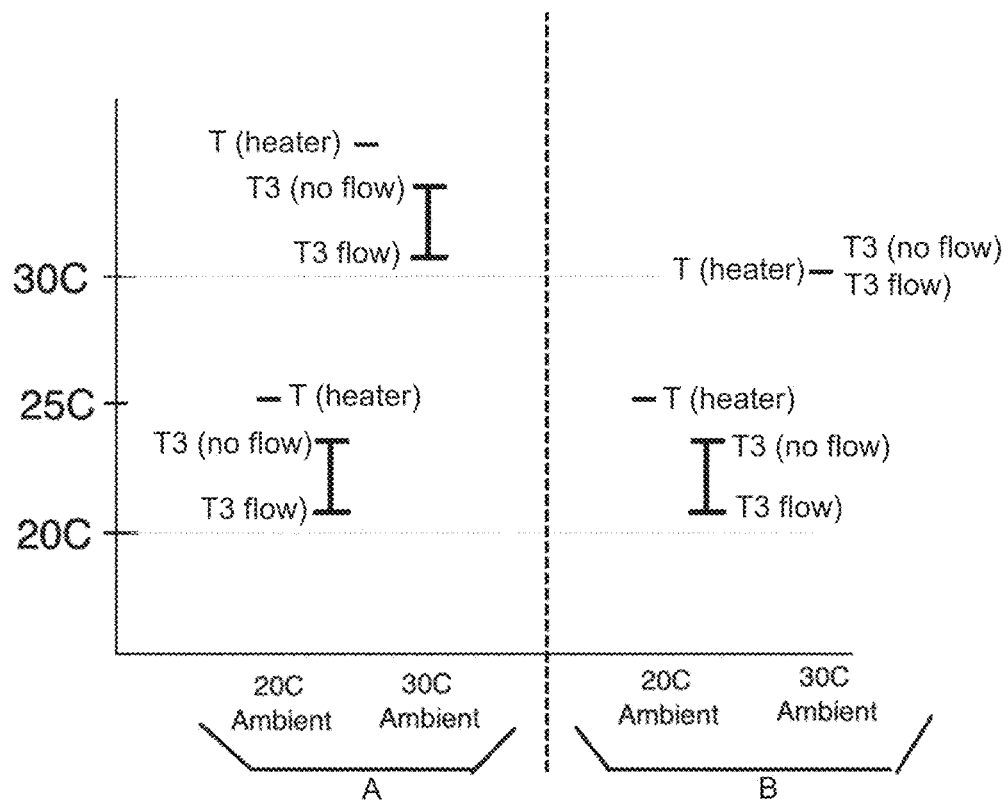
FIG. 12 illustrates the difference between using a constant power heater element (in accordance with embodiments of the present invention) and a constant temperature resistive heater element.

For the most consistent performance with variation in ambient temperature when operating at lower power settings, it is preferable that the heater dissipate a constant power, not operate at a constant temperature. With constant power dissipation, any change in ambient temperature will result in the same change of temperature for both the heater element 22 and the temperature sensor T3. This is not the case if a resistive heater were controlled to a fixed temperature setpoint, where, in an extreme example for illustration purposes only, if the ambient temperature were to rise above the heater temperature setpoint then the heater would no longer have the desired effect of heating the fluid inside the tubing above ambient. This is illustrated in FIG. 12. FIG. 12 illustrates the difference between using a constant power heater element (in accordance with embodiments of the present invention) and a constant temperature resistive heater element.

The left half (A) corresponds to a case of constant power dissipation from a heater. The right half (B) corresponds to a case of constant temperature output from the heater.

The left half (A) shows the temperature of the heater element ("T (heater)") and the temperature of sensor T3 both under flow ("T3 (flow)") and no-flow ("T3 (no flow)") conditions, when a constant power is dissipated in the heater. In this this case, changes in ambient temperature (x-axis) just shift all temperatures by the same amount.

The right half (B) shows the alternative case where a resistive heater is controlled to a constant temperature, such that if the ambient temperature rises above that setpoint the heater will turn off until temperature drops. This has the result that there is no change to sensor T3 between flow and no-flow conditions when the ambient temperature is higher than the setpoint temperature (in this case 30 degrees), as T3 and the heater will just sit at the ambient temperature. It would be possible to operate a constant temperature heater at a higher temperature (with the drawback of using more battery energy), but it will never have as much signal modulation as with a constant heater power arrangement.

The power dissipated in the heater is the product of the voltage times the current, or in a resistive heater element it is the voltage squared divided by the resistance. Near constant power dissipation in this heater can be achieved in a number of ways, outlined below.

In some examples, a resistive heater can be powered from a constant voltage or constant current supply in order to dissipate a constant power.

In some examples, if powered from a battery whose voltage drops as it is discharged, the battery chemistry can be chosen with the flattest discharge voltage curve to minimize the power change as it is discharged. For example, lithium chemistries would be preferred over alkaline chemistries as their voltage droops less as they are discharged.

In some embodiments, a pulse-width modulation technique can be used in conjunction with a hardware circuit or with microcontroller firmware that measures the supply voltage and adjusts the duty cycle of the heater to, on average, dissipate a constant power over the expected range of battery voltages.

Figure 13:
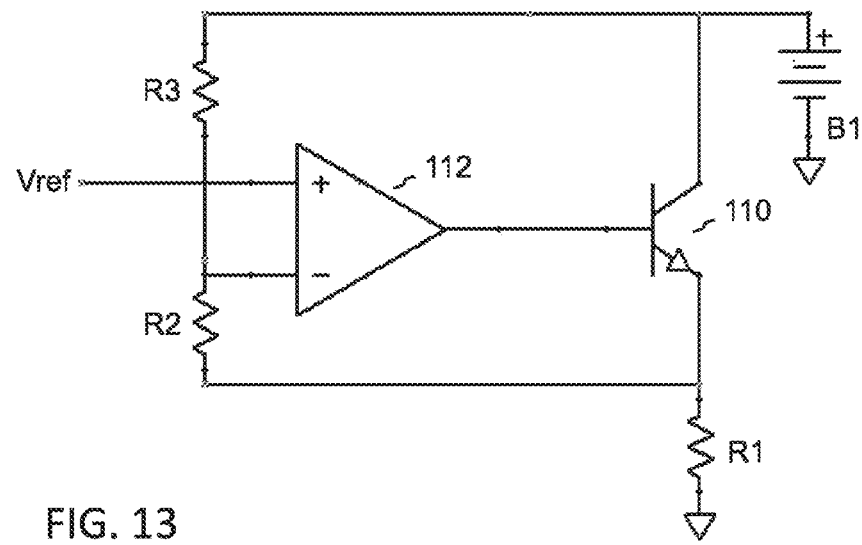
FIG. 13 shows an electronic circuit topology in which a power transistor is used as a heating element, and the power dissipated in the transistor remains approximately constant over the range of expected battery voltage.
Figure 14:
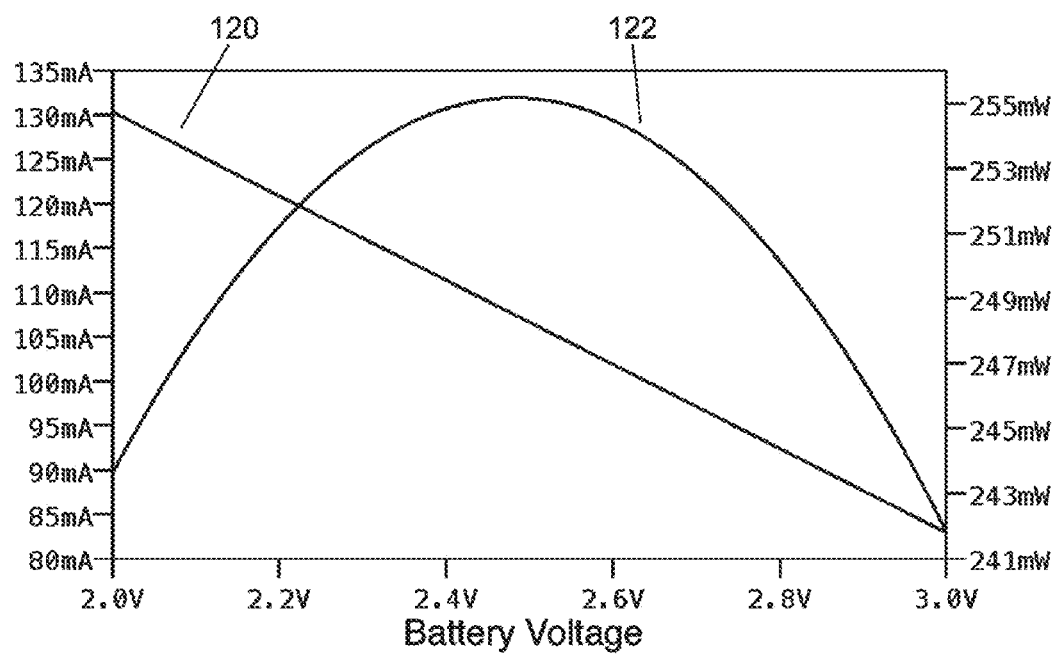
FIG. 14 shows a simulation output of a transistor heater element controlled for a near constant (0.25 Watt) power dissipation over the range of expected battery voltage.

In some embodiments, a power transistor with a heat-spreading pad can be used as the heater element. A circuit topology such as that shown in FIG. 13 can be used to drive the transistor 110 so that its power dissipation is nearly constant over the expected range of battery voltage, as shown in FIG. 14. Feedback to an operational amplifier 112 is the sum of a voltage component across the transistor 110 and a current component through it. This method was tested by the inventor in prototypes. With this arrangement, the power dissipated in the transistor 110 remains approximately constant despite changing battery (B1) voltage. FIG. 14 shows a simulation output of the transistor heater element controlled for a near constant (0.25 Watt) power dissipation over the range of expected battery voltage. The x-axis shows battery voltage. Line 120 shows the current in the transistor (y-axis, left). Line 122 shows the power dissipated in the transistor (y-axis, right).

In accordance with one or more embodiments, a preferred method for achieving a constant heating power by the heating element 22 is to use a pulse width modulation (PWM) technique.

For example, the device may comprise a local power source (e.g. a battery), and the controller may be adapted to convert an electrical output from the local power source into a pulse width modulated (PWM) electrical supply for driving the heating element, and to provide the pulse width modulated electrical supply to the heating element. The controller may be adapted to adjust a duty cycle of the PWM electrical supply in dependence upon the voltage of the power source so as to maintain a constant power dissipation in the heating element. This may in some cases mean maintaining a constant power input to the heating element (e.g. if the heating element is a heating resistor).

Figure 15:
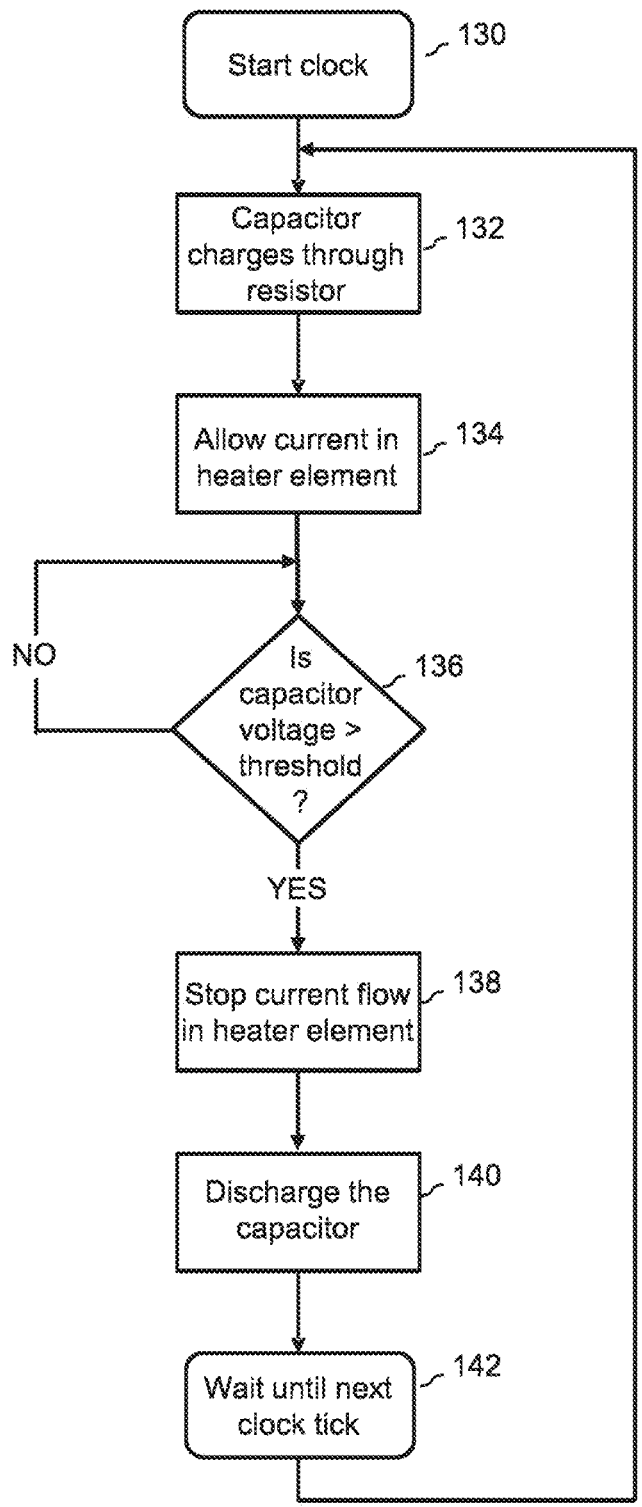
FIG. 15 illustrates steps of an example firmware algorithm to produce an approximately constant power in a resistive heater element as battery voltage changes, using a resistance-capacitance (RC) network to control pulse-width modulation (PWM) timing.

One advantageous set of embodiments may use a PWM technique to repeatedly charge a capacitor through a resistance connected to the battery voltage, where the resulting timing of the capacitor voltage is monitored using the algorithm shown in FIG. 15. This approach would be suitable if a microcontroller was not available.

FIG. 15 illustrates steps of an example firmware algorithm to produce an approximately constant power in a resistive heater element as battery voltage changes, using a resistance-capacitance (RC) network to control pulse-width modulation (PWM) timing.

The steps are as follows.

In step 130, a clock is started, for example with a with a 1 ms tick time/interval.

In step 132 a capacitor is allowed to charge through a resistor from the (e.g. battery) voltage source driving the heater.

In step 134, current is allowed through the heater element.

In step 136, it is determined whether the capacitor voltage exceeds a threshold. This decision step is looped until the result is YES, at which point, in step 138, current to the heater element is stopped. In step 140, the capacitor voltage is discharged to zero. The method then waits 142 until the next clock tick.

It can be seen that this will create a PWM scheme in which the pulse width will be automatically adjusted (via decision step 136) to provide an approximately constant power input to the heater.

Figure 16A:
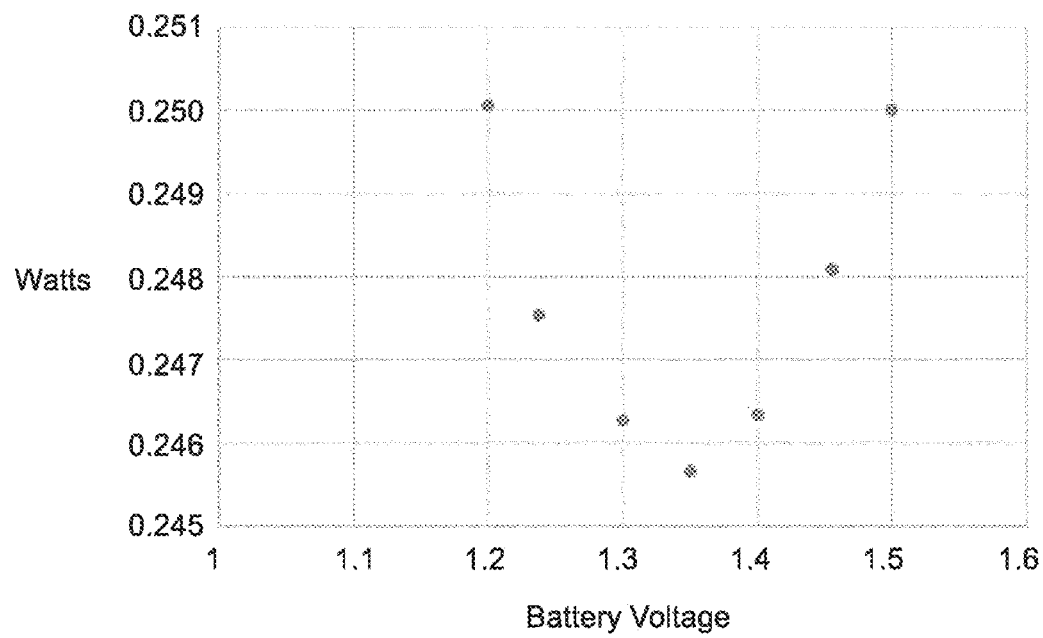
FIG. 16*a* shows a simulation output of the average power in a resistive heater element over a range of battery voltage using the firmware algorithm of FIG. 15.
Figure 16B:
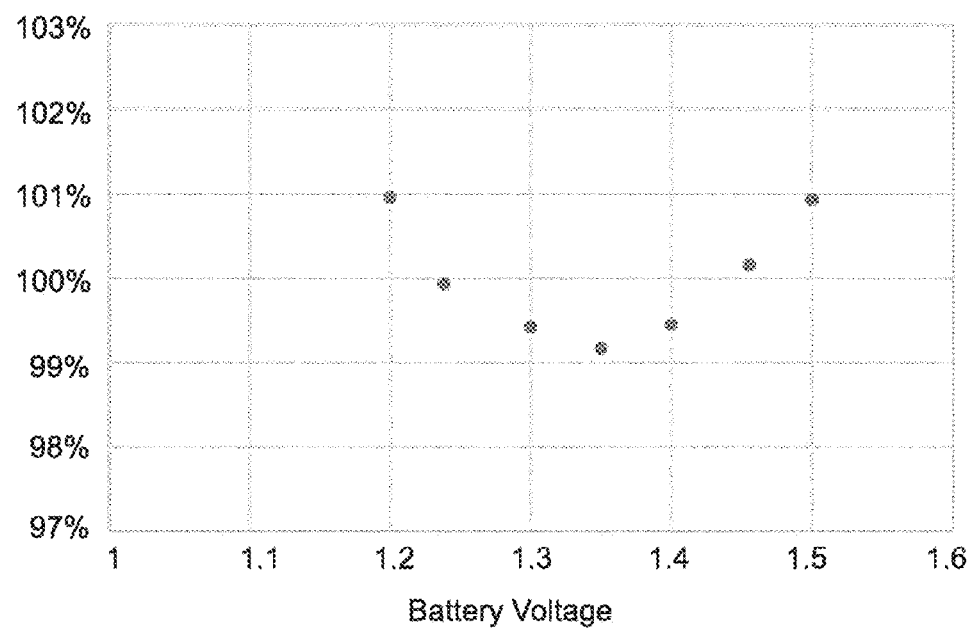
FIG. 16*b* shows a simulation output of the power in a resistive heater element, expressed as a percentage of nominal, over a range of battery voltage using the firmware algorithm of FIG. 15.

In this example, the power supply is a battery. The battery in this specific example is an Energizer L92 lithium cell whose cell potential ranges from 1.5 V to 1.2 V as it is discharged. The heater is a standard electronic resistor element of 5.49 Ohms, the RC time constant for the algorithm is 617 microseconds and the threshold voltage used in the algorithm is 0.945 V. FIG. 16a shows the resulting average heater power dissipation (y-axis, Watts) is approximately 0.25 Watts. FIG. 16b shows that the resulting heater power dissipation as the battery voltage (x-axis) declines varies by less than approximately +/−1%. Without this method (or something with equivalent effect) the heater power variation would be +/−18% over the same range of battery voltage.

As mentioned briefly above, in accordance with one or more embodiments, the device may be adapted to generate a user-perceptible alert to signal flow stoppage, and wherein a delay is imposed between detecting flow stopping and generating the alert, for example of approximately 60 seconds.

By way of background, it has been realized by the inventor that certain neurovascular procedures reveal another important limitation of traditional flow monitoring methods: they report a flow stoppage immediately. This is not consistent with the workflow of such procedures. It is normal in neurovascular procedures for there to be three to six bags of anticoagulant (and sometimes more) being infused into the patient simultaneously, each in a different catheter at a different vascular access port. During the procedure, the clinician selectively turns certain infusions off and then back on as different tools are repeatedly introduced and then removed from the catheters. If one of the infusions is turned off for more than 1 minute there is a serious risk to the patient of blood clot formation in the catheter and resulting stroke. With the various different tubing lines being turned off and then on, it is easy for the doctor to lose track of which lines are stopped and for how long. If a device is configured to provide a flow alarm that sounds immediately upon flow stoppage, this simply adds to the workflow clutter since flow stoppage in a line is intentional so long as it lasts no longer than 1 minute.

What a doctor in fact requires is to be alerted in case of an exception to proper practice, for example sound an alarm only if one tubing line is shut off for more than 30 seconds so the doctor can react to resume flow at less than the 1 minute time point. This would mean that alarms would be rare, and only occur if an actual problem exists. However, when flow is restarted the alarm should stop immediately, since in this case the problem has been cleared. Thus it is a realization of the inventor that there would be significant benefit in providing an asymmetrical delay: a delay when flow stops before creating an alert, but no delay when clearing the alert.

Depending upon the clinical scenario, different specific asymmetrical delay times may be appropriate, such as if infusions are disrupted during patient transport or during home care. However the principle is applicable in all scenarios: namely, generate an alert in the event that further delay could harm the patient, but stop the alert immediately when flow resumes.

There are existing thermal methods to measure flow and direction of flow in infusion tubing, but they do not provide asymmetrical delay time in reporting the stop of flow and immediately detect and report the resumption of flow.

Thus, in accordance with one or more embodiments, the controller may be adapted to generate an alert signal after a pre-set non-zero time delay following detecting flow stopping, and to terminate the alert signal immediately responsive to detecting flow starting. The alert signal may be a user-perceptible alert signal, e.g. a sensory output.

Figure 17:
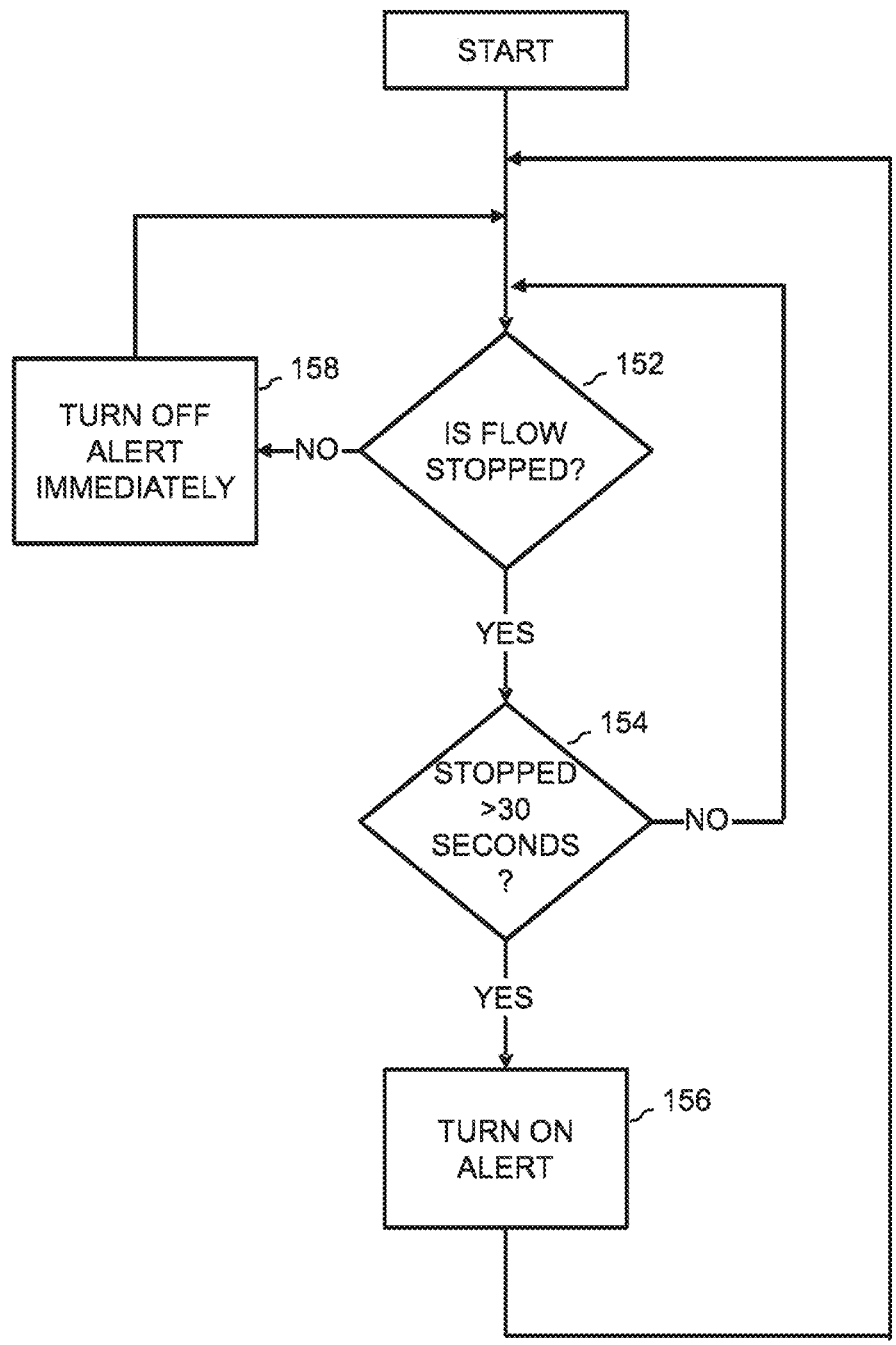
FIG. 17 is an example algorithm showing an asymmetrical delay introduced when starting an alert following detecting flow stoppage and no delay when clearing an alert following detecting flow restarting.

By way of example, FIG. 17 shows an example algorithm for introducing an asymmetrical delay when starting an alert following detecting flow stoppage and no delay when clearing an alert following detecting flow restarting.

The algorithm comprises a step 152 of detecting whether liquid fluid is flowing in the infusion tubing or not, for example based on any of the techniques discussed in this disclosure. If flow has stopped, a further decision step 154 assesses whether a pre-set time delay has passed (e.g. 30 seconds in the illustrated example). Once the time delay has passed, the alarm is activated 156. The method then returns to checking whether flow is still stopped. As soon as flow restarts, the alarm is deactivated 158 immediately. The time delay of step 154 may be set, by way of example, in the range of 20 seconds to 10 minutes or more, typically with a time in the 30-60 second range. When fluid flow is restored, the alarm condition is cleared promptly without delay.

It is noted that for a device adapted only to make a binary detection of a flow/no flow condition, the circuitry can be made simpler and the device physically smaller than prior art devices that seek to quantify an actual rate of flow.

As briefly mentioned above, the technical advantages of the device can be further enhanced in accordance with one or more embodiments by providing means for compressing a section of the tubing when the device is attached thereto, to reduce the radial distance between the heater and the sensor.

In particular, according to one or more embodiments, the device includes a means for applying a compression to the tubing wall when the housing is coupled to the tubing, wherein the compression reduces a radial distance between the first contact area and the second contact area. The compression is for example a squeezing action. The compression results in inward deformation (crushing) of the tube at the axial location of the heater 22 and temperature sensor T3, so that they are brought radially closer together.

The means for applying a compression may be adapted such that coupling the housing to the tubing has the effect of causing the compression to be applied.

In preferred embodiments, the means for applying the compression is provided by the housing, wherein the housing is structured such that, when coupled to the tubing, the compression is applied by the housing to the tubing wall.

Figure 18:
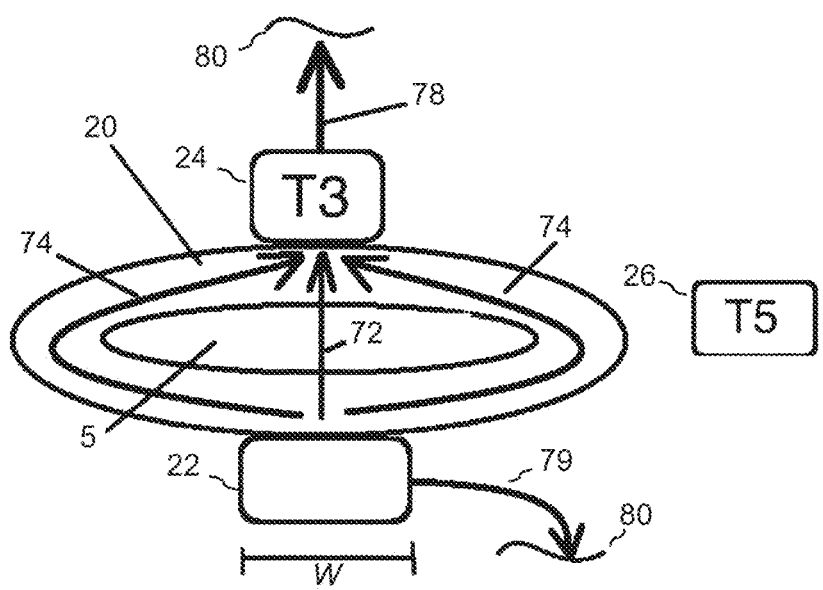
FIG. 18 shows an example device comprising means to apply an artificial flattening of the tubing through compression to decrease the radial thermal path length between heater and temperature sensor.

FIG. 18 illustrates the same arrangement as in FIG. 7, but wherein a compression has been applied as described above so that tubing is flattened at the axial location of the heating element 22 and the temperature sensor T3. This decreases the thermal path length (path 72) radially through the fluid from the heater within the lumen of the tubing, and moreover decreases this radial thermal path length as a ratio of the circumferential thermal path length 74 through the wall of the tubing. This therefore also decreases thermal interference via thermal conduction through the wall 20.

Introducing an intentional deformation of the tubing wall has a number of benefits, outlined below.

First, it shortens the thermal path length 72 radially through the fluid between the heater 22 and the sensor T3 so that radial path 72 becomes a more significant influence on the temperature at T3. This has the beneficial effect of increasing the thermal signal at T3.

Second, it results in the temperature sensor at T3 heating more quickly when flow stops because there is just a smaller volume of fluid between the heater and T3, so there is less fluid in that region to heat up. This has the effect of reducing the response time between flow stop and detection of flow stop by means of an inflection in the temperature signal.

Third, it likewise has the result that the temperature sensor at T3 responds more quickly to resumption of fluid flow due to the shortened radial path length 72. By way of example, this can also have the benefit that any "flow stopped" alarm can be cleared quickly. This can be seen in FIG. 10, where the signal drops immediately and precipitously when flow starts (point 106).

Fourth, it makes the system very sensitive to very slow flow rates, such as for the TKO ('to keep open') lines discussed previously, because it reduces the volume of fluid between the heater and T3. Even very slow flow rates will sweep the small volume of fluid out quickly and replace it with fresh fluid.

Figure 19:
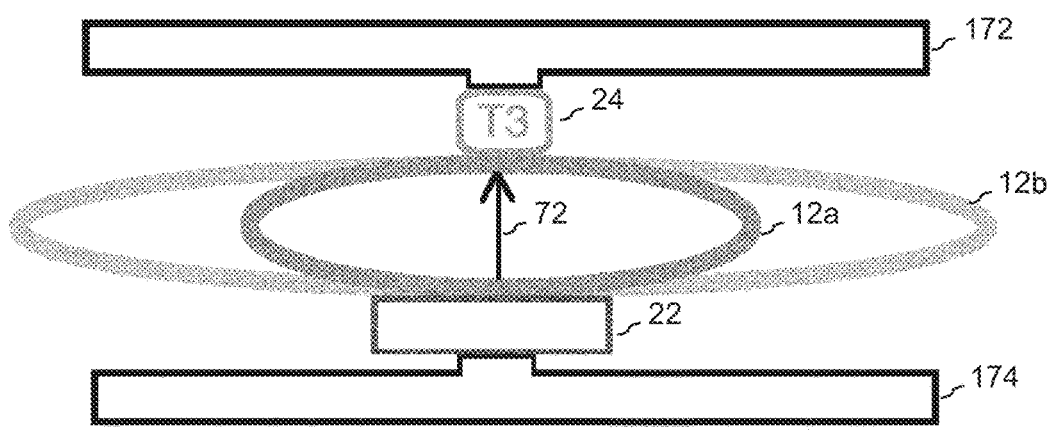
FIG. 19 is a cross sectional view of an example device adapted to receive and position different diameter sizes of tubing between a heater and temperature sensor, such that they have a same thermal path length radially.

Fifth, it can in some cases be a useful means for making the device performance consistent when working with a variety of tubing diameters. In particular, if the tubing compression is achieved by two plates that, in operation, are a fixed specific distance apart, then the radial thermal path length 72 between the heater and T3 will be constant, regardless of the initial diameter of the tubing. This principle is illustrated in FIG. 19 which illustrates a means for applying a compression to the tubing 12 in the form of a pair of opposing plates 172, 174, which might be accommodated in the housing in such a way that when the housing is coupled to the tubing 12, the tubing is received between the plates, and the plates are set at a pre-defined spacing apart from one another, which may be smaller than an expected minimum diameter of tubings with which the device is to be used. This has the effect of applying a compression to received tubing which results in a consistent radial path length 72 between the heater 22 and sensor T3 regardless of the initial diameter of the tubing. For example, FIG. 19 schematically illustrates two different tubings 12*a*, 12*b* of different diameters within the device.

By way of further illustration, one particular example device built as a prototype by the inventor will now be discussed. The details of this device do not limit the scope of the overall inventive concept and are provided by way of illustrative example.

A breadboard SENSOR MODULE was constructed to test the method of flow detection. The materials and equipment were as set out in Table 1 below:

TABLE 1

| | |
|---|---|
| VOLTAGE_SOURCE 1 | Leader LPS-151 |
| VOLTAGE_SOURCE 2 | Power Designs Model 5020 |
| VOLTMETER | Fluke 189 |
| HEATER_RESISTOR | Yaego RSF200JB-73-200R |
| THERMISTOR T1 | EPCOS B57540G0104F000 |
| THERMISTOR T3 | EPCOS B57540G0104F000 |
| FOAM BOARD | Elmer's Products, Inc. #950109 |
| IV BAG | Hospira 7951-12 |
| IV tubing set | Millpledge HB06536A |
| Timer | Radio Shack 63-1601 |

Construction of the device was as follows. A 5 mm thick foam board was initially cut into multiple pieces 202 approximately 150 mm long and 38 mm wide. Then multiple pieces 202*a*, 202*b*, 202*c*, . . . , 202*n* were stacked together as shown in the side cross-sectional view FIG. 20 and end cross sectional view FIG. 21.

Figure 20:
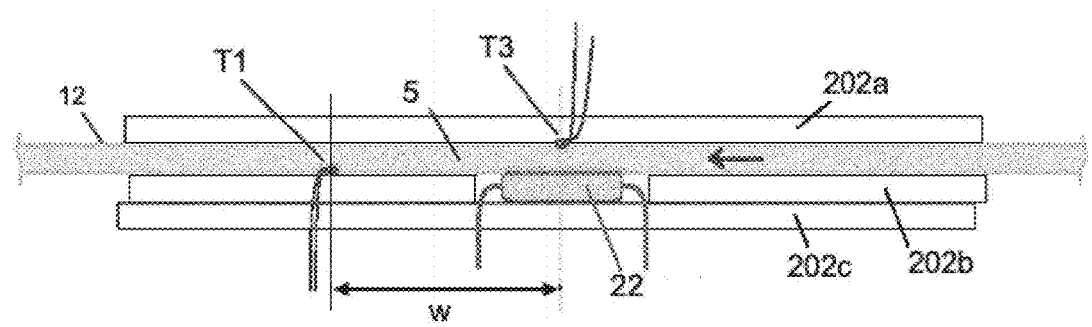
FIG. 20 is a cross sectional side view of a prototype device.
Figure 21:
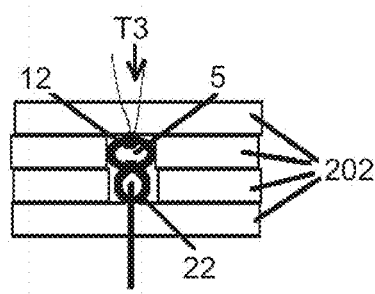
FIG. 21 is a cross sectional end view of the prototype device of FIG. 20.

A pocket was cut in one foam board piece 202*b* to accept the body of the resistor (indicated at 22). The wire leads of the resistor 22 were punched through to exit the bottom foam board. Another piece of the foam board was cut in two longitudinally to create a channel down the middle to accept the IV tubing 12. Two thermistors T1, T3 were placed as shown in FIG. 20, squeezed between the compliant IV tubing 12 and the foam board 202. The wire leads of thermistor T1 were punched through to exit the bottom foam board. The wire leads of thermistor T3 were punched through to exit the top foam board. The whole assembly was held together with adhesive tape.

Figure 22:
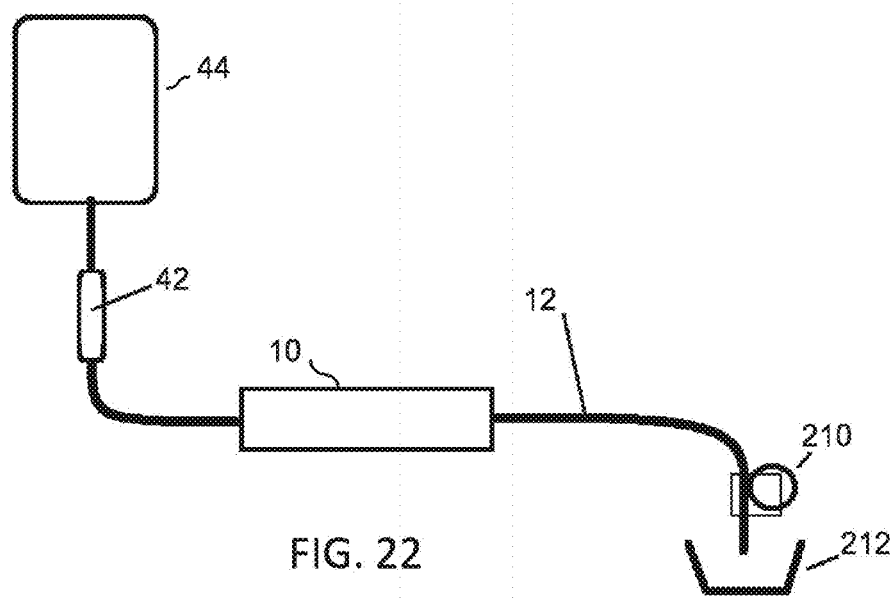
FIG. 22 is a schematic diagram of an example fluid path in operation.

FIG. 22 shows a schematic of the fluidic layout. An IV bag 44 was filled with tap water and hung upright with a drip chamber 42 hanging vertically below it. The tubing exited the drip chamber and then travels through the sensor module 10 and then through an adjustable shutoff valve 210, and then to a waste bucket 212. The shutoff valve can be adjusted to control the flow rate as measured by the number of drops per second visible in the drip chamber. This value can be set to completely stop the flow. The calibration of the particular drip chamber used is 60 drops per milliliter, or 17 microliters per drop.

The electrical circuitry shown in FIG. 9*a*, and discussed above, was used.

FIG. 9*a* shows the electrical connections, with the resistor 22 powered from a 7.0V power supply called VOLTAGE_SOURCE_1 so that the resistor dissipates approximately 0.25 Watt of power. A VOLTMETER was used to measure the voltage between points A and B. The VOLTAGE_SOURCE_2 was a precision adjustable power supply whose output voltage was adjusted to give 1.00V on the VOLTMETER across A-B when fluid flow was stopped; VOLTAGE_SOURCE_2 ended up being set to 2.61V to make this happen.

A measurement procedure was performed comprising stopping all fluid flow and then adjusting VOLTAGE_SOURCE_2 to produce 1.00V from A-B. Then flow was started at about 1 drop per second in the drip chamber and the voltage across A-B was measured and recorded after it equilibrated. Flow was increased to approximately 2 drops per second and the voltage across A-B was measured and recorded after sufficient time passed for it to equilibrate.

The results are as follows:

Voltage when fluid flow is stopped: 1.00 V
Voltage at 1 drop/second rate: 0.81 V
Voltage at 2 drop/second rate: 0.81 V The next measurement procedure was to measure the response time. An experimental threshold of 0.90 V was used as the point where flow is considered to have started or to have stopped. If flow is established and then flow is stopped, after some period of time which might be termed "Time to Alarm" the voltage from A to B will rise above the 0.90 V threshold. If flow has been stopped and then flow is restarted again, after some period of time that might be called "Time to Clear" the voltage from A to B will drop below the 0.90 V threshold. The objective was to measure how long it takes before an alarm condition is measured (the Time to Alarm) after flow becomes stopped, and how long it takes to clear an alarm after flow is resumed. Two trials were performed under the same conditions. The flow rate when flowing was approximately 1.4 drops per second.

The results are as follows:

Trial 1—Time to Alarm: 37 seconds
Trial 1—Time to Clear: 4 seconds
Trial 2—Time to Alarm: 35 seconds
Trial 2—Time to Clear: 4 seconds.

This shows that it takes a little more than half a minute after flow stops before it can be determined that there is a problem with flow being stopped. Note that in a device, this time can be easily extended to a longer time by triggering another delay before an alarm is reported to a user. This delay can be provided in firmware or by other means such as an analog or digital timer. So, for example, an alarm can be delayed so that an alarm will not be given to the user until 1 minute has passed with no flow. This data also shows that once flow resumes the alarm can be cleared quickly, in only a few seconds. If an alarm is given to the user and the user makes changes to the tubing to restart flow, the device should then respond quickly to any flow that starts up and proceed to clear the alarm.

Figure 23A:
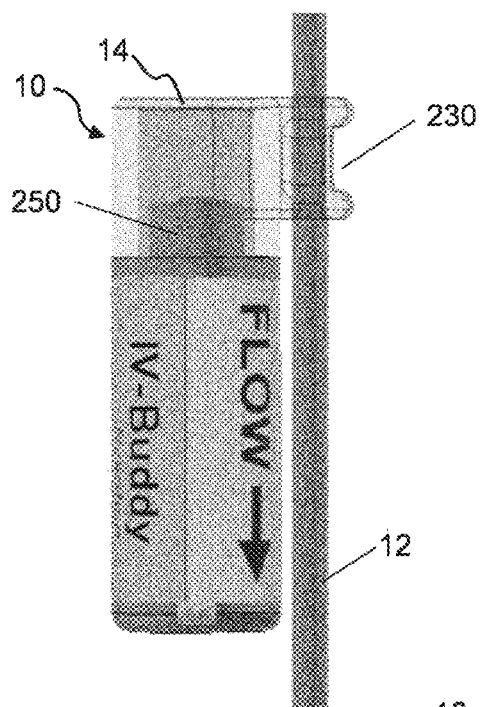
FIGS. 23*a* and 23*b* provide an exterior side elevational view and a side cross-sectional view, respectively, of an example device according to one or more embodiments.
Figure 23B:
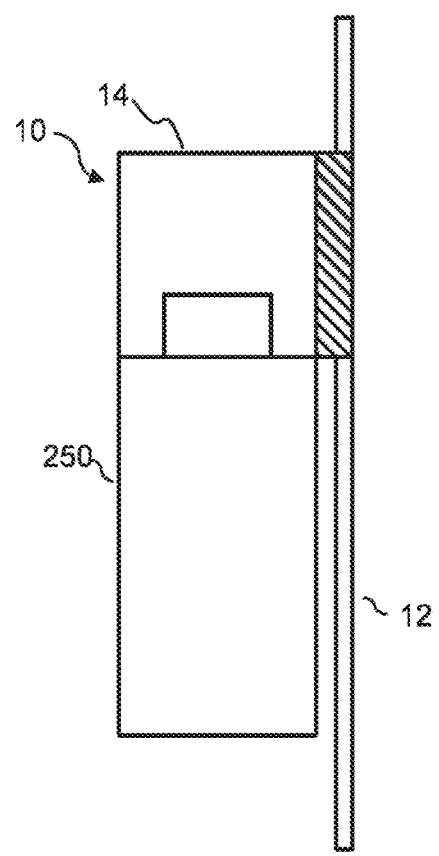

By way of illustration, FIG. 23a shows an exterior side elevational view of an example device according to one or more embodiments, and FIG. 23b shows a side cross-section through the same example device. This example device comprises a heater and sensor arrangement as shown in FIG. 2 or FIG. 3, with only one temperature sensor touching the tubing. As a consequence, the section of the device which touches the tubing (indicated at 230) can be very short, as it only needs to touch the tubing at one point. There is no need for the additional length that would be required if a channel were used to accept and hold the tubing against multiple sensors that are axially displaced along the tubing. This allows the device to be very compact. The size of the housing pieces that close over the tubing need only be big enough to allow the user's fingers to conveniently close the housing. FIG. 23a shows the size of this part relative to the size of a single AAA battery 250 which is used to power the device. The housing 14 of the device in this example is not much larger than the battery 250, wherein the housing accommodates the battery inside, and retention means for holding the housing and battery mechanically coupled together. The battery electrically connects to the device at an electrical connection site inside the housing.

A variety of further optional features which may be incorporated in one or more embodiments will now be discussed.

Typically, the device may be used in environments where ionic liquids such as saline, blood and urine are present. Most of the electronics can be sealed, and seals can keep the bulk of interfering liquids away from the heater and temperature sensor to avoid extraneous thermal pathways. However, in advantageous embodiments, the device may be designed so as to be resistant to the electrical effects of any residual interfering liquids that may reach the heater 22 or temperature sensor 24.

Any electrical traces that are under soldermask are protected from ionic liquid contamination. However, if surface mount chip devices are used for the temperature sensor and heater then these will have exposed electrical connection pads. Experiments were performed to measure the typical electrical resistance of a drop of a potential interfering ionic liquid on exposed 0805 (Imperial) surface mount pads on a printed circuit board, when energized with about 1 V. The results were as follows:

Saline (1×PBS): 6-12 megohms.
Blood: about 6 megohms.
Urine: 1.4-4 megohms.

The error when measuring temperature under these conditions should be insignificant, such as less than 0.1 degree C. If a thermistor temperature sensor chip with exposed terminals is used, the above measurements give an expectation of about 1 megohm of shunt resistance when ionic contaminants are present. Thus the thermistor may need to be 4K Ohms at room temperature to have an error from shunt leakage of 0.4% which is approximately an error of 0.1 degree C. for a typical thermistor that changes about 4% per degree C. A lower value such as 1K Ohms would give additional margin.

A resistive heater element will have resistance of less than this when powered from a battery so this contamination will not significantly change its resistance.

In accordance with one or more embodiments, temperature sensor 28, T4 shown in FIG. 4 may be used to compensate the algorithm for fluid that enters the inlet at a temperature different than ambient temperature. For example, in blood donation situations the inlet temperature may be closer to body temperature and thus higher than ambient temperature, or if the IV bag has been refrigerated, the inlet temperature may be lower than ambient temperature. The value of T4 can be used to adjust the value of the temperature measured at the other sensors to compensate for the inlet temperature difference. The amount of this adjustment depends on the thermal resistances between the different sensors. It is noted that this thermal resistance depends upon the fluid flow rate. For example, if the temperature T4 is greater than T5 then the measured value of T5 could be adjusted upwards somewhat to compensate for a higher inlet temperature. An alternative arrangement would be to position temperature sensor T5 to measure the temperature of the tubing at position T4, rather than ambient temperature elsewhere, to automatically compensate for inlet fluid temperatures that are different than ambient.

Power is consumed by the heater element and if the device is battery powered then attention needs to be paid to how long the battery will last. For some applications such as home healthcare, battery run time may be extended by periodically turning off the heater to save some power, and then turning it on to make the measurement and then turning it off again. The degree to which this duty cycle technique can be used depends upon how quickly the heater warms the tubing and the time constant of the thermal path between the heater and the temperature sensor when flow is stopped. For example, if it takes 2 minutes for the temperature sensor reading to equilibrate once the heater is turned on, and if it is acceptable to check for flow only once every 5 minutes, then the heater may be kept off for 3 minutes then turned on, and two minutes after that the temperature is measured to determine if there is flow and the results reported. Then the heater is turned off again and the cycle repeated. In that example the power dissipated in the heater has been reduced to 40% of the power if the heater were to run continuously, and the battery run time extended by approximately 2.5 times.

The "alarm" or "alert" mentioned earlier in this disclosure may take several possible forms. Audible or visual alarms are possibilities. Another possibility is wireless communication of the flow results to other devices or to a central monitoring center. Wireless can for example be in the form of microwave, radio, infra-red or other optical communication, ultrasonic or other acoustic communication. Mechanical alarms are possible either to activate an indicator or to actuate or trigger another device. Alarm indicators that are silent (e.g. haptic) could be of benefit in military applications where flashing lights or noisy beeps that could give away a soldier's position are too dangerous in combat environments.

An alternative or additional way to report the stoppage of fluid flow is to report to the user the length of time that flow has been stopped. Practitioners of the art can readily design a readout that will display that time in seconds or other time-related units. Users of the device can then use their professional judgement to evaluate the consequences of the time duration of that stoppage of flow in the situation at hand.

Note that in this disclosure, the word "cooler"/"cooling element" may be substituted for the word "heater"/"heating element" in any of the description above and, if so, then the polarity of the decision thresholds should be adjusted appropriately. The idea is that the temperature of the fluid is modified at one point and then the influence of that temperature change is measured across the tubing on the opposing side.

The methods discussed here are not limited to medical products but are applicable to any liquid fluid flow situation, such as veterinary applications or applications in agriculture or as an embedded sensor in other products such as automobiles.

An aspect of the invention also provides a method for sensing fluid flow through an infusion or effusion tubing line, comprising: holding a heating element in contact with an outside wall of the tubing at a first contact area; simultaneously holding a temperature sensor in contact with the outside wall of the tubing at a second contact area, wherein the second contact area is substantially radially opposite the first contact area across the lumen of the tubing; controlling the heating element such that it dissipates a substantially constant heating power; sensing a temperature output from the temperature sensor while the heating element is active; detecting a flow parameter or condition of fluid in the tubing based on an output from the temperature sensor.

The method may in some embodiments further comprise compressing the tubing at the location of the heater and temperature sensor so as to reduce a radial distance between the first contact area and second contact area. In some embodiments, the force applied to compress the tubing simultaneously acts to hold the temperature sensor and heater in contact with the tubing at the first and second contact areas.

Embodiments described above provide a thermally-based mass-flow sensor. As already discussed above, various embodiments may comprise a combination of one or more of the following advantageous features.

In some embodiments, the controller is adapted to perform only a binary flow detection: is there flow, yes or no? It may not include functionality for quantitating the rate of flow, which thereby simplifies operation and reduces the required number of temperature sensors.

In some embodiments, responsive to detecting flow stopping the controller may generate a user-perceptible alert following a delay of a specific amount of time, and responsive to detecting flow restarting, the controller may immediately report the restart (e.g. by deactivating the alarm).

The temperature sensor is located substantially radially opposite the heater. This optimizes the sensor position to respond quickly when flow resumes, for example in order to promptly clear a reported flow stoppage.

The optimized sensor position also allows the device to be physically smaller than prior art devices, an advantage in the intended use cases.

In some embodiments, the shape of the tubing is intentionally distorted by the device to reduce the radial distance between the heater and the sensor, to thereby further optimize the response time of the temperature sensor, and improve the sensitivity to very low flow rates and adapt the system to a range of tubing diameters.

According to example circuit designs discussed above, the design of the electronic circuits for temperature sensing can be implemented at very low cost in a compact package.

Further aspects of the invention are recited by the following numbered clauses.

1. A device that non-invasively abuts the outside of tubing to detect and indicate when fluid flow has stopped or started using a thermal mass-flow technique, with a heater element touching one side wall of the tubing and a temperature sensor touching the radially opposed side wall of the tubing to determine if fluid flow has stopped or started.
2. The device of clause 1 wherein compensation for variation in ambient temperature is provided by a second temperature sensor not in contact with the tubing.
3. The device of clause 1 where compensation for variation in ambient temperature is provided by a second temperature sensor in contact with the tubing (for example arranged upstream from the heater).
4. The device of clause 1, where the heater dissipates a constant power as the power supply voltage changes.
5. The device of clause 1, where the tubing is deformed by compression in the region between the heater element and the temperature sensor so as to shorten the thermal path length through the fluid.
6. The device of clause 1, where the performance is consistent across a range of tubing diameters (i.e. the device is operable to couple to a range of tubing diameters).
7. The device of clause 1, where electrical impedance levels are chosen to be insensitive to contamination by ionic liquids.
8. The device of clause 1, further comprising an additional temperature sensor T4 for measuring fluid temperature upstream from the device, e.g. at an inlet location.
9. The device of clause 1, wherein the indication is a light.
10. The device in clause 1 where the indication is a sound. The device in clause 1 where the indication is a visual readout of the time that fluid flow has been stopped.
11. The device in cause 1 where the indication is a mechanical movement.
12. The device in clause 1 where the indication is a wireless communication to another device.

As discussed above, embodiments make use of a controller. The controller can be implemented in numerous ways, with software and/or hardware, to perform the various functions required. A processor is one example of a controller which employs one or more microprocessors that may be programmed using software or firmware (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

The controller referred to in this disclosure may comprise a single control/processing component or an assembly of control/processing components. Thus, steps described as carried out by the controller may be carried at by a plurality of control or processing components in some cases.

Examples of controller components that may be employed in various embodiments of the present disclosure include, but are not limited to, conventional microprocessors, application specific integrated circuits (ASICs), configurable logic devices and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to". Any reference signs in the claims should not be construed as limiting the scope.

The invention claimed is:

1. A device for sensing a fluid flow through an infusion or effusion tubing line, comprising:
a housing adapted to removably couple to an outside wall of the tubing line;
the housing accommodating a heating element and a first temperature sensor; and
a controller operatively coupled to the heating element and the first temperature sensor;
wherein the housing is adapted to hold the heating element in contact with an outside wall of the tubing line at a first contact area when the housing is coupled to the tubing line, and hold the first temperature sensor in contact with the outside wall of the tubing line at a second contact area when the housing is coupled to the tubing line, the second contact area substantially radially opposite the first contact area across the lumen of the tubing line when the housing is coupled to the tubing line, and
wherein the controller is adapted to simultaneously:
control the heating element to dissipate a substantially constant heating power; and
detect a flow parameter or condition based on an output from the first temperature sensor.

2. The device of claim 1, wherein
the device further includes a second temperature sensor, when the housing is coupled to the tubing line, the second temperature sensor is positioned for sensing either: an ambient temperature of the air in the environment of the device, or a temperature of the fluid at a location upstream from the heating element, at a location substantially uninfluenced by the thermal output of the heating element; and
the controller is adapted to detect the flow parameter or condition based on outputs of both the first temperature sensor and the second temperature sensor, based on compensating a temperature change measurement of the first temperature sensor using temperature change measurements of the second temperature sensor.

3. The device of claim 1, wherein the device further comprises a local power source for electrically powering the heating element.

4. The device of claim 1, wherein the controlling of the heating element to dissipate a substantially constant heating power comprises driving the heating element with a constant power supply.

5. The device of claim 4,
wherein the device comprises a local power source, and
wherein the controller is adapted to convert an electrical output from the local power source into a pulse width modulated (PWM) electrical supply for driving the heating element, and to provide the pulse width modulated electrical supply to the heating element, and
wherein the controller is adapted to adjust a duty cycle of the PWM electrical supply in dependence upon the voltage of the electrical output from the power source so as to maintain a constant power dissipation in the heating element.

6. The device of claim 1, wherein the controller is adapted to detect a flow stop/start condition based at least in part on sensing variations in an output from the first temperature sensor while the heating element is being controlled.

7. The device of claim 1, wherein the controller is adapted to generate an alert signal after a pre-set non-zero time delay following detecting flow stopping, and to terminate the alert signal immediately responsive to detecting flow starting.

8. The device of claim 1, wherein the device includes means for applying a compression to the outside wall of the tubing line when the housing is coupled to the tubing line, wherein the compression reduces a radial distance between the first contact area and the second contact area.

9. The device of claim 8, wherein the means for applying a compression is adapted such that coupling the housing to the tubing line has the effect of causing the compression to be applied.

10. The device of claim 8, wherein the means for applying a compression is provided by the housing, wherein the housing is structured such that, when coupled to the tubing line, the compression is applied by the housing to the outside wall of the tubing line.

11. The device of claim 1, wherein the housing comprises first and second parts, the first part accommodating the heating element and the second part accommodating the first temperature sensor, and the housing is operable to couple to the tubing line by moving the housing into a closed position with the tubing line trapped between the first and second parts, and the housing is structured to accommodate the tubing line when the housing is in the closed position, and to hold the heating element and first temperature sensor at the first and second contact areas.

12. The device of claim 1, wherein the device further includes at least one further temperature sensor arranged, when the housing is coupled to the tubing line, to be held against the outside wall of the tubing line at a position axially displaced from the heating element, and wherein the controller is further operatively coupled with the at least one further temperature sensor, and wherein the controller is adapted to determine a flow rate and/or direction using the first temperature sensor and the further temperature sensor.

13. The device of claim 1, wherein the housing is adapted for coupling to an infusion line having an outside diameter between 3 mm and 10 mm.

14. The device of claim 1, wherein the housing is adapted to permit coupling to infusion lines of a range of different outside diameters.

15. The device of claim 1, wherein the device is a standalone device.

16. A method for sensing fluid flow through an infusion or effusion tubing line, comprising:
- holding a heating element in contact with an outside wall of the tubing line at a first contact area;
- simultaneously holding a first temperature sensor in contact with the outside wall of the tubing line at a second contact area, wherein the second contact area is substantially radially opposite the first contact area across the lumen of the tubing line;
- controlling the heating element such that the heating element dissipates a substantially constant heating power;
- sensing a temperature output from the first temperature sensor while the heating element is active; and
- detecting a flow parameter or condition of fluid in the tubing line based on an output from the first temperature sensor.

17. The method of claim 16, wherein the method further comprises compressing the tubing line at the location of the heater and first temperature sensor so as to reduce a radial distance between the first contact area and the second contact area.

18. The method of claim 17, wherein the force applied to compress the tubing line simultaneously acts to hold the first temperature sensor and the heater in contact with the tubing line at the first and second contact areas.

* * * * *